US007691572B2

(12) United States Patent
Heneine et al.

(10) Patent No.: US 7,691,572 B2
(45) Date of Patent: Apr. 6, 2010

(54) METHOD AND KIT FOR DETECTING RESISTANCE TO ANTIVIRAL DRUGS

(75) Inventors: Walid M. Heneine, Atlanta, GA (US); Gerardo Garcia-Lerma, Decatur, GA (US); Shinji Yamamoto, Kumamoto (JP); William M. Switzer, Stone Mountain, GA (US); Thomas M. Folks, Atlanta, GA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 394 days.

(21) Appl. No.: 11/054,023

(22) Filed: Feb. 9, 2005

(65) Prior Publication Data

US 2005/0170339 A1 Aug. 4, 2005

Related U.S. Application Data

(60) Division of application No. 10/190,101, filed on Jul. 3, 2002, now abandoned, which is a continuation-in-part of application No. 09/719,906, filed as application No. PCT/US99/13957 on Jun. 18, 1999, now Pat. No. 6,787,126.

(60) Provisional application No. 60/090,051, filed on Jun. 19, 1998.

(51) Int. Cl.
*C12Q 1/70* (2006.01)
*A61K 39/21* (2006.01)

(52) U.S. Cl. .................................. 435/6; 424/208.1

(58) Field of Classification Search .................. None
See application file for complete search history.

(56) References Cited

U.S. PATENT DOCUMENTS

| 5,576,177 | A | 11/1996 | Fridland et al. |
| 5,631,128 | A | 5/1997 | Kozal et al. |
| 5,849,494 | A | 12/1998 | Heneine et al. |
| 6,136,934 | A | 10/2000 | Reuven et al. |
| 6,787,126 | B1 * | 9/2004 | Heneine et al. ............... 424/9.1 |

FOREIGN PATENT DOCUMENTS

| WO | WO 93 23574 | 11/1993 |
| WO | WO 96 23076 | 8/1996 |
| WO | WO 97 27319 | 7/1997 |

OTHER PUBLICATIONS

Adje of al., "High Prevalence of Genotypic and Phenotypic HIV-1 Drug-Resistant Strains among Patients Receiving Antiretroviral Therapy in Abidjan, Cote d'Ivoire," *J. Acquired Immune Deficiency Syndromes* 26:501-506 (2001).
Arion et al., "Phenotypic Mechanism of HIV-1 Resistance to 3'-Azido-3'-deoxythymidine (AZT): Increased Polymerization Processivity and Enhanced Sensitivity to Pyrophosphate of the Mutant Viral Reverse Transcriptase," *Biochemistry* 37:15908-15917 (1998).

Arts and Wainberg, "Mechanisms of Nucleoside Analog Antiviral Activity and Resistance during Human Immunodeficiency Virus Reverse Transcription," *Antimicrob. Agents Chemother.* 40(3):527-540 (Mar. 1996).
Carroll et al., "Sensitivity of HIV-1 Reverse Transcriptase and Its Mutants to Inhibition by Azidothymidine Triphosphate," *Biochemistry* 33:2113-2120 (1994).
De Jong et al., "Insertion of two amino acids combined with changes in reverse transcriptase containing tyrosine-215 of HIV-1 resistant to multiple nucleoside analogs," *AIDS* 13:75-80 (1999).
Frenkel et al., "Specific, Sensitive, and Rapid Assay for Human Immunodeficiency Virus Type 1 *pol* Mutations Associated with Resistance to Zidovudine and Didanosine," *J. Clin. Microbiol.* 33(2):342-347 (Feb. 1995).
Garcia-Lerma et al., "A Rapid Non-Culture-Based Assay for Clinical Monitoring of Phenotypic Resistance of Human Immunodeficiency Virus Type 1 to Lamivudine (3TC)," *Antimicrobial Agents and Chemotherapy* 43(2):264-270 (Feb. 1999).
Garcia-Lerma et al., "Measurement of Human Immunodeficiency Virus Type 1 Plasma Virus Load Based on Reverse Transcriptase (RT) Activity: Evidence of Variabilities in Levels of Virion-Associated RT," *J. Infect. Dis.* 177:1221-1229 (1998).
Garcia-Lerma et al., "Quantitation of Human Immunodeficiency Virus Type 1 Group O Load in Plasma by Measuring Reverse Transcriptase Activity," *J. Clin. Micro.* 2000; 38(1):402-405 (2000).
Garcia-Lerma et al., "Susceptibility of Human T Cell Leukemia Virus Type 1 to Reverse Transcriptase Inhibitors: Evidence for Resistance to Lamivudine," *J. Infect. Dis.* 184:507-510 (2001)(electronically published Jul. 25, 2001).
Gulick et al., "Treatment with Indinavir, Zidovudine, and Lamivudine in Adults with Human Immunodeficiency Virus Infection and Prior Antiretroviral Therapy," *N. Engl. J. Med.* 337(11):734-739 (1997).
Havlir et al., "Nevirapine-Resistant Human Immunodeficiency Virus: Kinetics of Replication and Estimated Prevalence in Untreated Patients," *J. Viro.* 70(11):7894-7899 (Nov. 1996).
Heneine et al., "Detection of Reverse Transcriptase by a Highly Sensitive Assay in Sera from Persons Infected with Human Immunodeficiency Virus Type 1," *J. Infect. Diseases* 171:1210-1216 (1995).
Hertogs et al., "A Rapid Method for Simultaneous Detection of Phenotypic Resistance to Inhibitors of Protease and Reverse Transcriptase in Recombinant Human Immunodeficiency Virus Type 1 Isolates from Patients Treated with Antiretroviral Drugs," *Antimicrobial Agents and Chemotherapy* 42(2):269-276 (Feb. 1998).

(Continued)

*Primary Examiner*—Stacy B Chen
(74) *Attorney, Agent, or Firm*—Gifford, Krass, Sprinkle, Anderson & Citkowski, P.C.

(57) ABSTRACT

Assays and kits for the detection of phenotypic resistance of a retrovirus to reverse transcriptase inhibitor-drugs in a biological sample. The assays are based on the direct analysis of the susceptibility of retroviral reverse transcriptase to inhibition by a reverse transcriptase inhibitor drug. The enzymatic activity of the reverse transcriptase is determined by measuring the DNA product produced when an RNA template and a first complementary DNA primer from a suitable region of the encephalomyocarditis virus genome are incubated with a biological sample containing reverse transcriptase in the presence of the drug to which resistance is being determined. The DNA product is amplified and detection of the amplified DNA indicates resistance to the drug employed in the assay. Detection of relatively greater amounts of amplified DNA when certain drugs are used indicates the presence of multiple nucleoside analog resistant strains or mutations.

15 Claims, 7 Drawing Sheets

OTHER PUBLICATIONS

Kavlick et al., "Genotypic and phenotypic characterization of HIV-1 isolated from patients receiving (—) -2',3'-dideoxy-3'-thiacytidine," *Antiviral Research* 28:133-146 (1995).

Kavlick et al., "Emergence of Multi-Dideoxynucleoside-Resistant Human Immunodeficiency Virus Type 1 Variants, Viral Sequence Variation, and Disease Progression in Patients Receiving Antiretroviral Chemotherapy," *J. Infect. Dis.* 98:1506-1513 (Jun. 1998).

Kerr et al., "Pre-Steady-State Kinetic Characterization of Wild Type and 3'-Azido-3'-deoxythymidine (AZT) Resistant Human Immunodeficiency Virus Type 1 Reverse Transcriptase: Implication of RNA Directed DNA Polymerization in the Mechanism of AZT Resistance," *Biochemistry* 36:14064-14070 (1997).

Krebs et al., "Single-Step Kinetics of HIV-1 Reverse Transcriptase Mutants Responsible for Virus Resistance to Nucleoside Inhibitors Zidovudine and 3-TC," *Biochemistry* 36:10292-10300 (1997).

Lacey et al., "Biochemical Studies on the Reverse Transcriptase and RNase H Activities from Human Immunodeficiency Virus Strains Resistant to 3'-Azido-3'-deoxythymidine," *J. Biol. Chem.* 267(22): 15789-15794 (Aug. 1992).

Larder et al., "Potential Mechanism for Sustained Antiretroviral Efficacy of AZT-3TC Combination Therapy," *Science* 269:696-699 (Aug. 1995).

Larder et al., "Multiple Mutationsin HIV-1 Reverse Transriptase Confer High-Level Resistance to Zidovudine (AZT)," *Science* 246:1155-1158 (1989).

Larder et al., "A Family of Insertion Mutations between Codons 67 and 70 of Human Immunodeficiency Virus Type 1 Reverse Transcriptase Confer Multinucleoside Analog Resistance," *Antimicrobial Agents and Chemotherapy* 43:1961-1967 (1999).

Larder et al., "HIV with Reduced Sensitivity to Zidovudine (AZT) Isolated During Prolonged Therapy," *Science* 243:1731-1734 (Mar. 1989).

Lennerstrand et al., "Correlation between Viral Resistance to Zidovudine (AZT) and Resistance at the Reverse Transcriptase Level for a Panel of Human Immunodeficiency Virus Type 1 Mutants," *J. Virology* 75:7202-7205 (2001).

Li et al., "Molecular Characterization of Human Immunodeficiency Virus Type 1 Cloned Directly from Uncultured Human Brain Tissue: Identification of Replication-Competent and Defective Viral Genomes," *J. Virol.* 65(8):3973-3985 (Aug. 1991).

Maeda et al., "Altered drug Sensitivity, Fitness, and Evolution of Human Immunodeficiency Virus Type 1 with pol Gene Mutations Conferring Multi-Dideoxynucleoside Resistance," *J. Infect. Dis.* 177:1207-1213 (May 1998).

Mas et al., "Role of a dipeptide insertion between codons 69 and 70 of HIV-1 reverse transcriptase in the mechanism of AZT resistance," *EMBO J.* 19(21):5752-5761 (2000).

Mellors et al., "Mutations in HIV-1 Reverse Transcriptase and Protease Associated with Drug Resistance," *International Antiviral News* 3(1):8-13 (Jan. 1995).

Meyer et al., "A Mechanism of AZT Resistance: an Increase in Nucleotide-dependent primer Unblocking by Mutant HIV-1 Reverse Transcriptase," *Mol. Cell* 4:35-43 (1999).

Miller et al., "Antiviral activity of tenofovir (PMPA) against nucleoside-resistant clinical HIV samples," *Nucleosides Nucleotides Nucleic Acids* 20:1025-1028 (2001).

Mouroux et al., "Conditions of selection of "thymidine analog mutations" (TAMs) in naive patients receiving different antiretroviral combinations including d4T," *Pathology Biology* 48:508-512 (2000)(English Abstract).

Mulder et al., "Rapid and Simple PCR Assay for Quantitation of Human Immunodeficiency Virus Type 1 RNA in Plasma: Application to Acute Retroviral Infection," *J. Clin. Microbiol.* 32(2):292-300 (Feb. 1994).

Nguyen et al., "Resistance of Human Immunodeficiency Virus Type 1 to Acyclic 6-Phenylselenenyl- and 6-Phenylthiopyrimidines," *Antimicrobial Agents and Chemotherapy* 38(10):2409-2414 (Oct. 1994).

Petropoulos et al., "A Novel Phenotypic Drug Susceptibility Assay for Human Immunodeficiency Virus Type 1," *Antimicrobial Agents and Chemotherapy* 44(4):920-928 (Apr. 2000).

Qari et al., "Susceptibility of the porcine endogenous retrovirus to reverse transcriptase and protease inhibitors," *J. Virology* 75:1048-1053 (2001).

Richman et al., "Human immunodeficiency virus type 1 mutants resistant to nonnucleoside inhibitors of reverse transcriptase arise in tissue culture," *Proc. Natl. Acad. Sci. USA* 88:11241-11245 (Dec. 1991).

Schinazi et al., "Mutations in retroviral genes associated with drug resistance," *International Antiviral News* 4(6):95-107 (1996).

Schinazi et al., "Selective Inhibition of Human Immunodeficiency Viruses by Racemates and Enantiomers of cis-5-Fluoro-1-[2-(Hydroxymethyl)-1,3-Oxathiolan-5-yl]Cytosine," *Antimicrobial Agents and Chemotherapy* 36(11):2423-2431 (Nov. 1992).

Schmit et al., "Multiple Drug Resistance to Nucleoside Analogues and Nonnucleoside Reverse Transcriptase Inhibitors in an Efficiently Replicating Human Immunodeficiency Virus Type 1 Patient Strain," *J. Infect. Dis.* 174:962-968 (1996).

Schmit et al., "Multiple dideoxynucleoside analogue-resistant (MddNR) HIV-1 strains isolated from patients from different European countries," *AIDS* 12:2007-2015 (1998).

Shafer et al., "Drug Resistance and Heterogeneous Long-Term Virologic Responses of Human Immunodeficiency Virus Type 1-Infected Subjects to Zidovudine and Didanosine Combination Therapy," *J. Infect. Dis.* 172:70-78 (Jul. 1995).

Shirasaka et al., "Changes in drug sensitivity of human immunodeficiency virus type 1 during therapy with azidothymidine, dideoxycytidine, and dideoxyinosine: An in vitro comparative study," *Proc. Nat. Acad. Sci.* USA 90:562-566 (1993).

Shirasaka et al., "Emergence of human immunodeficiency virus type 1 variants with resistance to multiple dideoxynucleosides in patients receiving therapy with dideoxynucleosides," *Proc. Natl. Acad. Sci.* USA 92:2398-2402 (Mar. 1995).

Sluis-Cremer et al., "Molecular mechanisms of HIV-1 resistance to nucleoside reverse transcriptase inhibitors (NRTIs)," *Cell. Mol. Life Sci.* 57:1408-1422 (2000).

Stuyver et al., "Line Probe Assay for Rapid Detection of Drug-Selected Mutations in the Human Immunodeficiency Virus Type 1 Reverse Transcriptase Gene," *Antimicrobial Agents and Chemotherapy* 41(2):284-291 (Feb. 1997).

Ueno et al., "Comparative Enzymatic Study of HIV-1 Reverse Transcriptase Resistant to 2',3'-Dideoxynucleotide Analogs Using the Single-Nucleotide Incorporation Assay," *Biochemistry* 36: 1092-1099 (1997).

Ueno et al., "Enzymatic Characterization of Human Immunodeficiency Virus Type 1 Reverse Transcriptase Resistant to Multiple 2',3'-Dideoxynucleoside 5'-Triphosphates," *J. Biol. Chem.* 270(40):23605-23611 (Oct. 1995).

Van Laethem et al., "Patient HIV-1 strains carrying the multiple nucleoside resistance mutations are cross-resistant to abacavir," *AIDS* 14:469-471 (2000).

Van Vaerenbergh et al., "Prevalence and Characteristics of Multinucleoside-Resistant Human Immunodeficiency Virus Type 1 among European Patients Receiving Combinations of Nucleoside Analogues," *Antimicrobial Agents and Chemotherapy* 44:2109-2117 (2000).

Vazquez-Rosales et al., "Rapid Screening of Phenotypic Resistance to Nevirapine by Direct Analysis of HIV Type 1 Reverse Transcriptase Activity in Plasma," *AIDS Research and Human Retroviruses* 15:1191-1200 (1999).

Wainberg et al., "Development of HIV-1 resistance to (—)2'-deoxy-3'-thiacytidine in patients with AIDS or advanced AIDS-related complex," *AIDS* 9:351-357 (1995).

Weinstock et al., "Prevalence of Mutations Associated with Reduced Antiretroviral Drug Susceptibility among Human Immunodeficiency Virus Type 1 Seroconverters in the United States, 1993-1998," *J. Infect. Dis.* 182:330-333 (2000).

Winters et al., "A 6-Basepair Insert in the Reverse Transcriptase Gene of Human Immunodeficiency Virus Type 1 Confers Resistance to Multiple Nucleoside Inhibitors," *J. Clin. Invest.* 102:1769-1775 (1998).

Yamamoto et al., "Highly sensitive qualitative and quantitative detection of reverse transcriptase activity: optimization, validation, and comparative analysis with other detection systems," *J. Virol. Methods* 61:135-143 (1996).

* cited by examiner

PATIENT N12

PATIENT N06

PATIENT N07

SEQUENCE LISTING

```
<160> NUMBER OF SEQ ID NOS: 4

<210> SEQ ID NO 1
<211> LENGTH: 20
<212> TYPE: DNA
<213> ORGANISM: Encephalomyocarditis Virus

<400> SEQUENCE: 1
cattagccat ttcaacccat                                              20

<210> SEQ ID NO 2
<211> LENGTH: 24
<212> TYPE: DNA
<213> ORGANISM: Encephalomyocarditis Virus

<400> SEQUENCE: 2
gttcatgaca ggccgataca gagg                                         24

<210> SEQ ID NO 3
<211> LENGTH: 25
<212> TYPE: DNA
<213> ORGANISM: Encephalomyocarditis Virus

<400> SEQUENCE: 3
tgctctcacc ttatcaaaat ccaat                                        25
```

-continued

```
<210> SEQ ID NO 4
<211> LENGTH: 374
<212> TYPE: DNA
<213> ORGANISM: Encephalomyocarditis Virus

<400> SEQUENCE: 4
cauuagccau uucaacccau gcguuugagg agaagcgcuu ucugauaacc gguggucucc      60
caucagguug ugcagcgacc ucaaugcuaa acacuauaau gaauaauaua auaauuaggg     120
cggguuugua ucucacguau aaaaauuuug aauuugauga ugugaaggug uugucguacg     180
gagaugaucu ccuuguggcc acaaauuacc aauuggauuu ugauaaggug agagcaagcc     240
ucgcaaagac aggauauaag auaacucccg cuaacacaac uucuaccuuu ccucuuaauu     300
cgacgcuuga agacguuguc uucuuaaaaa gaaaguuuaa gaaagagggc ccucuguauc     360
ggccugucau gaac                                                       374
```

METHOD AND KIT FOR DETECTING RESISTANCE TO ANTIVIRAL DRUGS

This application is a divisional of U.S. application Ser. No. 10/190,101, filed Jul. 3, 2002, entitled "Method and Kit for Detecting Resistance to Antiviral Drugs," which is incorporated herein by reference in its entirety. U.S. application Ser. No. 10/190,101, now abandoned, is a continuation-in-part and claims priority to U.S. application Ser. No. 09/719,906 filed Jun. 18, 200 (now U.S. Pat. No. 6,787,126), which is incorporated herein by reference in its entirety and which was a national phase application of PCT Application Ser. No. PCT/US99/13957, filed Jun. 18,1999, which claimed priority to U.S. Provisional Application Ser. No. 60/090,051, filed Jun. 19,1998.

This invention was made by the Centers for Disease Control and Prevention, an agency of the United States Government. The government may have certain rights in this invention.

TECHNICAL FIELD

The present invention relates in general to assays for detecting resistance of a retrovirus to reverse transcriptase inhibitor therapies and/or to characterizing the nature of the resistance. More specifically, in one aspect, the invention relates to non-culture, polymerase chain reaction-based phenotypic assays for detecting antiviral drug-resistant reverse transcriptase activity in a sample from a patient infected with a retrovirus. In a second aspect, the invention relates to non-culture, polymerase chain reaction-based phenotypic assays for characterizing the nature of antiviral drug-resistant reverse transcriptase activity in a sample from a patient infected with a retrovirus.

BACKGROUND OF THE INVENTION

One of the most ravaging diseases of the late twentieth century has been AIDS (acquired immunodeficiency syndrome), brought on by HIV (human immunodeficiency virus) infection. Currently, there are no cures for this disease and minimally effective treatments. One of the problems that exist in the development of therapies for HIV infection is that the HIV virus rapidly develops resistance to a wide variety of chemotherapeutic agents. HIV, particularly human immunodeficiency virus type 1 (HIV-1), mutates over time to become resistant to many of the antiviral drugs administered for treatment. AIDS physicians need to know when the antiviral therapy being used to treat a individual patient is no longer effective so that the antiviral drug or drug combination can be modified, thereby minimizing viral replication and the onset of immunodeficiency symptoms.

Reverse transcriptase (RT) inhibitors such as zidovudine (ZDV, also referred to as azidothymidine (AZT)), didanosine (ddI or dideoxyinosine), zalcitabine (ddC or dideoxycytosine), lamivudine (3TC), stavudine (d4T), and nevirapine (NVP) are nucleoside or non-nucleoside analogs currently approved for the treatment of HIV-1 infections. 3TC is known to have potent anti-HIV-1 activity and minimal toxicity, and is one of the most commonly used drugs in combination therapy as first-line treatment for HIV-1-infected patients. 3TC administered in combination with AZT provides greater and more sustained increases in $CD4^+$ cell counts, and higher reductions in HIV-1 RNA viral load than continued AZT or 3TC monotherapy. 3TC in combination with AZT and protease inhibitors slows the progression of HIV-1 disease and reduces levels of HIV-1 RNA to less than 500 copies per milliliter for as long as one year in 90% of patients (Gulick et al., *N. Engl. J. Med.* 337: 734-739 (1997)).

However, the use of reverse transcriptase inhibitors, such as 3TC, in both monotherapy or combination therapy has resulted in the emergence of drug-resistant variants of HIV-1 (Gulick et al., *N. Engl. J Med.* 337: 734-739 (1997)). For a drug such as 3TC, the resistance is conferred by mutations in codon 184 of the HIV-1 reverse transcriptase gene, which replaces the wild type methionine residue (M; ATG) with a valine (V; GTG) via a transient substitution with an isoleucine (I; ATA). The presence of this M184V mutation has been associated with a greater than 500-fold resistance to 3TC and the partial loss of the anti-retroviral and clinical benefits of the drug. It is therefore important to monitor for drug resistance in individuals treated with reverse transcriptase inhibitors.

Phenotypic assays provide direct and definitive evidence of resistance to reverse transcriptase inhibitor drugs. However, presently available assays for the analysis of phenotypic resistance are based on virus culture and are therefore labor intensive and time consuming (two to five weeks), costly, and unsuitable for rapid clinical monitoring or surveillance of drug resistance (Kavlick et al., *Antiviral Research* 28: 133-146 (1995); Wainberg et al., *AIDS* 9: 351-357(1995)). In addition, these assays are fraught with biologic variabilities, including those related to viral isolation and tropism. Since tissue culture is highly selective for viral strains with in vitro growth advantages, these culture-based assay methods may not be representative of the total virus population present in vivo (Li et al., *J. Virol.* 65: 3973-3985 (1991)).

In the absence of rapid phenotypic assays, genotypic tests are currently being used to provide indirect evidence of resistance. Genotypic testing monitors for the presence of mutations that are associated with resistance, such as the M184V mutation. Among these genotypic tests, primer-specific PCR, point mutation, and reverse hybridization assays are the most commonly used (Wainberg et al., *AIDS* 9: 351-357(1995); Frenkel et al., *J. Clin. Microbiol.* 33: 342-347 (1995); Stuyver et al., *Antimicrob. Agents Chemother.* 41: 284-291 (1997)). Unfortunately, clinical monitoring of reverse transcriptase inhibitor drug resistance by genotypic testing may not detect unrecognized mutations or potential synergistic or antagonistic effects of complex mutation patterns arising from combination therapy with different reverse transcriptase inhibitors. For example, the suppression of phenotypic resistance to AZT conferred by the M184V mutation clearly illustrates the effect that a combination of mutations may have in a given phenotype (Larder et al., *Science* 269: 696-699 (1995)). Also, genotypic testing only detects resistance associated with known mutations (i.e., codon 184 for 3TC resistance).

U.S. Pat. No. 5,631,128 to Kozal describes polymerase chain reaction (PCR) assays for monitoring antiviral therapies in the treatment of AIDS. These genotypic assays use PCR to measure HIV-1 RNA copy number in plasma or to measure specific known HIV-1 RNA mutations, namely the mutation at codon 215 or codon 74 of the pol gene. The HIV-1 RNA copy number is an indication of the circulating HIV viral load. A decrease in HIV-1 RNA copy number correlates with successful antiretroviral therapy, whereas an increase in HIV-1 RNA copy number indicates disease progression, most likely caused by resistance to therapy. Therefore, the genotypic assays described in U.S. Pat. No. 5,631,128 detect only previously identified viral RNA mutations and are incapable of detecting phenotypic resistance caused by known or novel mutations, or the assays detect a rise in HIV-1 RNA copy number, which could be due to conditions other than resistance. An incorrect diagnosis of drug resistance followed by cessation of the antiviral therapy being administered could result in exacerbation of a disease that had been responding to therapy.

Therefore, there is a need for sensitive, rapid methods for the detection of HIV resistance to drug therapies in patients so that, if the virus becomes resistant to a particular drug or combination of drugs, the therapy can be modified, thereby keeping viral replication to a minimum and preventing or postponing the onset of AIDS.

SUMMARY OF THE INVENTION

An assay and kit for the detection of phenotypic resistance to a reverse transcriptase inhibitor drug in a biological sample is provided. Preferably, the biological sample is from a patient infected with a retrovirus. The assay is based on the direct analysis of the susceptibility of retroviral reverse transcriptase to inhibition by a reverse transcriptase inhibitor drug.

The enzymatic activity of the reverse transcriptase enzyme can be determined by measuring the DNA product produced when an RNA template and a first functionally complementary DNA primer are incubated with a biological sample containing reverse transcriptase in the presence of the drug to which resistance is being determined. In certain aspects, the drug can be a 5-triphosphate form of the nucleoside analog such as, by way of example, AZT triphosphate, and the assay can monitor the ability of the reverse transcriptase of interest to incorporate the drug into an extended DNA primer. As a control, the enzymatic activity of the reverse transcriptase enzyme can also be determined in the absence of the drug. In this case, the incubation mixture is reacted under conditions whereby the RNA template and the DNA primer will anneal and a first DNA strand will be synthesized as an extension from the DNA primer if the reverse transcriptase in the sample is resistant to and not inhibited by the drug. The first DNA product can be amplified using a second DNA primer that is functionally complementary to the first DNA product and suitable PCR reagents and conditions, and the amplified product detected in accordance with methods known to those skilled in the art. Detection of the amplified DNA indicates resistance to the drug employed in the assay. The difference in reverse transcriptase activity in the assays with and without drug verifies a finding of resistance and can provide an indication as to the degree of resistance to the drug. Use of 5'-triphosphate versions of nucleoside analogs can be used to determine the phenotypic resistance of viruses to non-triphosphate versions of nucleoside analogs. Other versions of nucleoside analogs that can be used as substrates for reverse transcriptase enzymes that result in extension of primers can also be used in the assay.

Primers and sequences to be used can be any that fulfill specific objectives of the assay when they are used as described herein or are recognized to be used by those of skill in the art. For example, the RNA template to be used can be any RNA sequence that fulfills the specific objective of the assay. Specifically, the RNA template used in the assay can be any template that when combined with appropriate primers, a reverse transcriptase and other components necessary for the function of reverse transcriptase can result in the synthesis of an DNA product wherein the DNA product's identity is directed by the sequence or base-pairing functionality of the RNA template. Further, the RNA template used in the assay can be such that when presented to a reverse transcriptase in the presence or absence of an inhibitor or drug that effects the reverse transcriptase's activity, the quantity of DNA product formed in the presence of the inhibitor or drug is effected to a degree that can be detected. Specifically, the primers to be used in the assay can be any primer that can hybridize to the provided RNA template or the first DNA product and that can be extended by a reverse transcriptase. Any such primer is a functionally complementary primer. As will be recognized by those of skill in the art, the level of complementary required will depend on the specific sequences of the primers and the sequences of the site of the RNA template or DNA products to which the primers bind to promote extension of products by required polymerase activity. Similarly, the level of DNA products formed can characterized as being relatively present or relatively absent wherein the characterization indicates that if products are detectable at levels significantly greater than what is deemed to be insignificant or greater than what is deemed to result when the characteristic being assayed for is not present. For example, in an assay of a reverse transcriptase conducted in the presence and absence of an inhibitor, if the formation of certain quantity of DNA product normally occurs if the reverse transcriptase is a resistant strain in the presence of the inhibitor or of the non-resistant reverse transcriptase in the absence of the inhibitor, then the amount of product produced is relatively present. Whereas, if the amount of DNA product present is an amount of DNA product formed in by a non-resistant reverse transcriptase in the presence of the inhibitor, then the amount of product produced is relatively absent.

The biological sample under investigation can be a biological fluid. The nature and characteristics of the biological sample can effect the quantity of sample used or preferred, although one of skill in the art can determine conditions and quantities required by practical considerations, such as, but not limited to, ease in handling, strength of relevant signal, concentration of analyte of interest and the like. For example, the biological sample can be a 0.5 µl to 1.0 ml sample of blood plasma or serum. The RNA template can be any template according to the requirements described above. Further, the RNA template can be an RNA template having minimal secondary content under conditions similar or identical to those used during the assay where extension of the first primer occurs. Minimal secondary structure as described herein includes any level of structure wherein the structure does not appreciably interfere with the rate of primer extension or does not diminish the synthesis of DNA product to such a level that addition of nucleoside analog inhibitors of the selected reverse transcriptase such that the resulting levels of product formed with or without the inhibitor are indistinguishable. Suitable examples of such RNA templates include RNA templates having characteristics selected from the group consisting of, less than 50% G-C content and little or no secondary structure. Preferably, the RNA template comprises sequence from an RNA virus. Preferably, the RNA template comprises sequence from an encephalomyocarditis virus. Preferred first and second DNA primers are functionally complementary primers as described. Preferably, the first and second DNA primers are complementary to regions in the RNA template and first DNA product, respectively. For instance, preferably, the RNA template consists of the ribonucleotide of SEQ ID NO:4 the first DNA primer consists of the oligonucleotide of SEQ ID NO:2 the second DNA primer consists of the oligonucleotide of SEQ ID NO:1 and PCR amplification is achieved by utilizing 30-40 cycles of heating the synthesized DNA and primer pair to 93° to 97° C. for 30 to 90 seconds, at 53° to 57° C. for 30 to 90 seconds, and at 70° to 74° C. for 30 to 90 seconds. The amplified synthesized DNA can be detected by hybridization to a detectable hybridization probe. The detectable hybridization probe can be an internal specific oligoprobe using an enzyme linked immunosorbent assay (ELISA), Southern blot hybridization methods, or similar methods.

Additionally provided is a kit for determining reverse transcriptase inhibitor drug resistance in a biological sample. The kit contains a suitable region of the encephalomyocarditis virus genome or nucleotide sequence corresponding to a suitable region of the encephalomyocarditis virus genome as an RNA template, a first complementary DNA primer for reverse transcriptase, and a second complementary DNA primer for amplification via the polymerase chain reaction, and the RT inhibitor or inhibitors under investigation, whereby each component is provided in separate containers or any combination of the components is provided in a single container. The kit may optionally contain the apparatus and one or more containers for obtaining and storing the sample prior to and during analysis and suitable buffers and other reagents to facilitate nucleic acid hybridization, synthesis, amplification and detection.

Therefore, it is an object of the present invention to provide sensitive methods for detecting drug resistance to reverse transcriptase inhibitor in a retrovirus-infected sample.

It is a further object of the present invention to provide methods for detecting the presence or absence of pathogen strains that are resistant to reverse transcriptase inhibitors. In certain aspects, it is a purpose to detect the presence of pathogen strains that are resistant to nucleoside analog reverse transcriptase inhibitors.

It is a further object of the present invention to provide a method for detecting drug resistance that is rapid, reliable, sensitive, and not labor intensive.

It is a further object of the present invention to provide a drug resistance assay that is phenotypic, not genotypic.

It is a further object of the present invention to provide an assay for drug resistance in which only a small amount of sample is needed for highly sensitive analysis.

It is a further object of the invention to provide an assay for the direct testing of biological body fluid samples such as serum, plasma, cerebrospinal fluid, saliva, semen and the like without extensive concentration, culturing or other processing techniques that would be required to increase the levels of reverse transcriptase in the sample under analysis.

It is a further object of the invention to provide an assay for drug resistance of a retrovirus that does not involve detection or amplification of the nucleic acid molecules of the retrovirus.

It is a further object of the invention to provide an assay to detect multiple nucleoside analog resistance (MNR) of a retrovirus wherein the assay includes incubating the retrovirus with a reverse transcriptase inhibitor antiviral drug that is a nucleoside analog, an RNA template, and a first functionally complementary DNA primer and detecting the presence or absence of a first DNA product, wherein the detection of the first DNA product indicates that the retrovirus has multiple nucleoside analog resistance. The retrovirus' multiple nucleoside analog resistance can be confirmed by repeating the assay with other nucleoside analog inhibitors. Preferably, the RNA template has minimal or no significant secondary structure. Preferably, the RNA template has less than 50% G-C content. Examples of such templates include RNA molecules having sequence from encephalomyocarditis virus such as SEQ ID NO:4 or RNA molecules having sequence similar to the sequence shown in SEQ ID NO:4. Sequence substantially the same as that shown in SEQ ID NO:4 can include significant numbers of additions, deletions or substitutions including 1, 2, 3, 4, 5, 7, 10, 20, 25, 30, 40, 50, 75, 100, 150or 200 additions, deletions, substitutions or combinations thereof.

It is a further object of the invention to provide a method for characterizing strains of HIV-1 as being MNR mutants and as being distinct from wild-type or classical reverse transcriptase mutant strains. The method includes; incubating a strain of HIV-1 with a reverse transcriptase inhibitor antiviral drug, an RNA template, and a first functionally complementary DNA primer and detecting the presence or absence of a first DNA product, wherein the detection of the first DNA product indicates that the strain of HIV-1 has multiple nucleoside analog resistance and is distinct from either wild-type or classical reverse transcriptase mutant strains. Preferably, the RNA template has minimal or no significant secondary structure. Preferably, the RNA template has less than 50% G-C content. Examples of such templates include RNA molecules having sequence from encephalomyocarditis virus such as SEQ ID NO:4 or RNA molecules having sequence similar to the sequence shown in SEQ ID NO:4. Sequence substantially the same as that shown in SEQ ID NO:4 can include significant numbers of additions, deletions or substitutions including 1, 2, 3, 4, 5, 7, 10, 20, 25, 30, 40, 50, 75, 100, 150or 200 additions, deletions, substitutions or combinations thereof.

It is a further object of the invention to provide a method for characterizing strains of HIV-2 as being MNR mutants and as being distinct from wild-type or classical reverse transcriptase mutant strains. The method includes; incubating a strain of HIV-2 with a reverse transcriptase inhibitor antiviral drug, an RNA template, and a first functionally complementary DNA primer and detecting the presence or absence of a first DNA product, wherein the detection of the first DNA product indicates that the strain of HIV-1 has multiple nucleoside analog resistance and is distinct from either wild-type or classical reverse transcriptase mutant strains. Preferably, the RNA template has minimal or no significant secondary structure. Preferably, the RNA template has less than 50% G-C content. Examples of such templates include RNA molecules having sequence from encephalomyocarditis virus such as SEQ ID NO:4 or RNA molecules having sequence similar to the sequence shown in SEQ ID NO:4. Sequence substantially the same as that shown in SEQ ID NO:4 can include significant numbers of additions, deletions or substitutions including 1, 2, 3, 4, 5, 7, 10, 20, 25, 30, 40, 50, 75, 100, 150or 200 additions, deletions, substitutions or combinations thereof.

It is a further object of the invention to provide a method for identifying the presence of retrovirus strains with mutations that confer multiple nucleoside analog resistance. The method includes; incubating a suspect sample with a reverse transcriptase inhibitor antiviral drug wherein the drug is a nucleoside analog, an RNA template, and a first complementary DNA primer, wherein the RNA template and first complementary DNA primer are oligonucleotides that comprise sequence corresponding to sequence from a region of the encephalomyocarditis virus genome having no significant secondary structure and less than 50% G-C content, and detecting the presence or absence of a first DNA product, wherein the detection of the first DNA product indicates the presence of retrovirus strains having multiple nucleoside analog resistance.

It is a further object of the invention to provide a method to identify the presence of retrovirus strains bearing classical reverse transcriptase mutations. The method includes identifying nucleoside analog resistant strains and testing the strains using a method that includes; incubating a sample containing a retrovirus strain with a reverse transcriptase inhibitor drug wherein the drug is a nucleoside analog, an RNA template, and a first complementary DNA primer and detecting the presence or absence of a first DNA product, wherein the absence of the first DNA product indicates the absence of a retrovirus strain having multiple nucleoside analog resistance and wherein this absence with the known resistance of nucleoside analog resistance of the tested strain indicates that the retrovirus strain has classical reverse transcriptase mutations. Preferably, the RNA template has minimal or no significant secondary structure. Preferably, the RNA template has less than 50% G-C content. Examples of such templates include RNA molecules having sequence from encephalomyocarditis virus such as SEQ ID NO:4 or RNA molecules having sequence similar to the sequence shown in SEQ ID NO:4. Sequence substantially the same as that shown in SEQ ID NO:4 can include significant numbers of additions, deletions or substitutions including 1, 2, 3, 4, 5, 7, 10, 20, 25, 30, 40, 50, 75, 100, 150 or 200 additions, deletions, substitutions or combinations thereof.

As will be understood by those of skill in the art, the putative inhibitors of reverse transcriptase and drugs can include nucleoside analogs and nucleoside analogs to be screened can be screened by use of forms of those drugs that mimic the naturally occurring nucleoside triphosphates, such as deoxyadenosine-5'-triphosphate, deoxycytosine-5'-triphosphate, deoxyguanosine-5'-triphosphate and deoxythymidine-5'-triphosphate. Examples of such variants of drugs include those such as phosphorothioates, phosphoramidates, or those wherein hydroxyl groups are replaced by functional groups known to the art such as, but not limited to, amino and sulfhydryls. Further, assays to determine the resistance or susceptibility of viral strains, species or variants to particular drugs can include testing of metabolites or active forms of those drugs that act as analogs of nucleoside-5'-triphosphates.

These and other objects, features, and advantages of the present method and kit will become apparent after a review of the following detailed description of the disclosed embodiments and the appended claims.

DETAILED DESCRIPTION OF THE DISCLOSED EMBODIMENTS

Figure 1A:
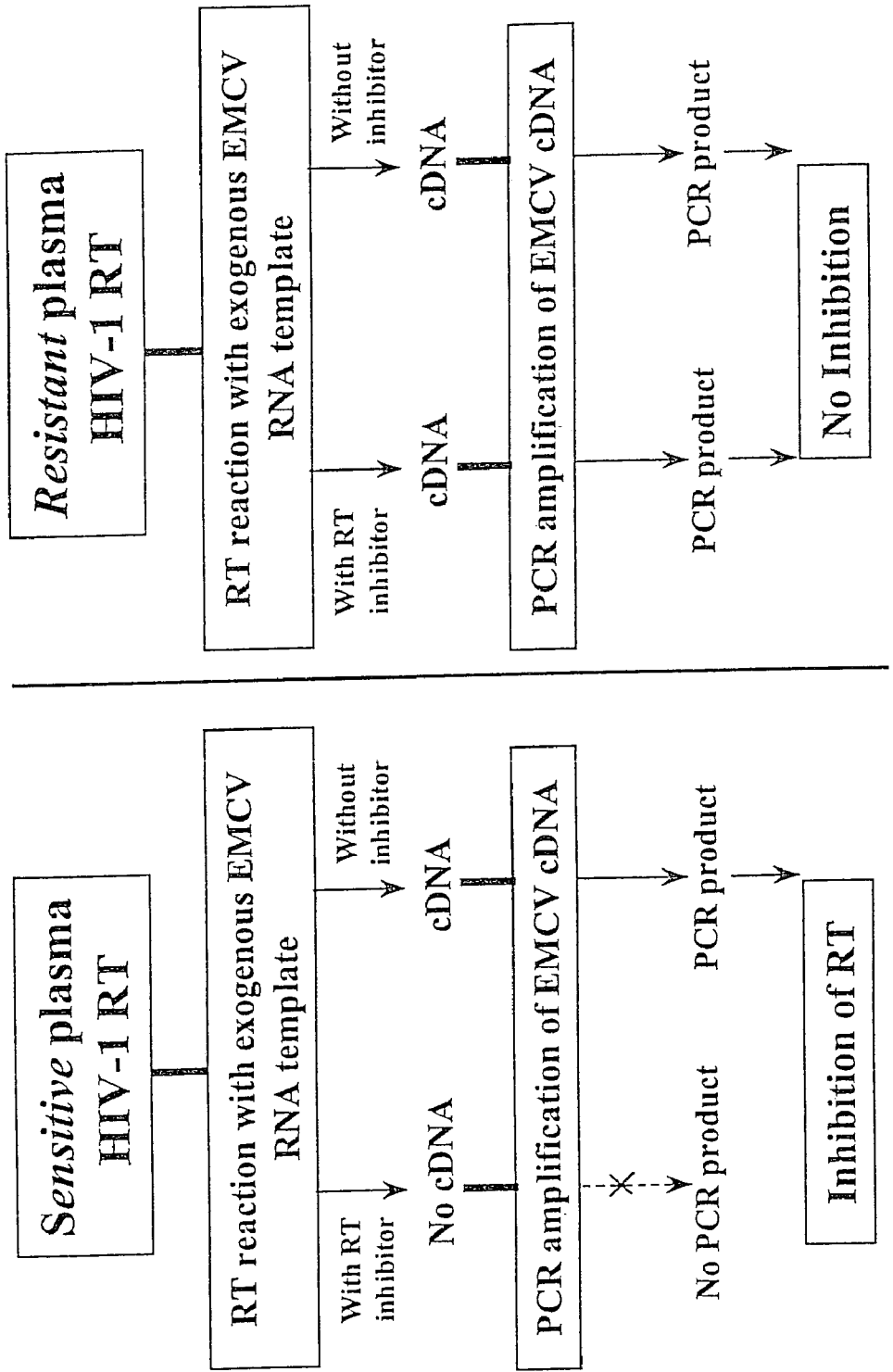
FIG. 1A is a flow chart depicting a phenotypic assay for the analysis of plasma HIV-1 resistance to reverse transcriptase antiviral drugs.

An assay and kit for the detection and monitoring of antiviral drug resistance of a retrovirus in a biological sample are provided. The assay is a non-culture, PCR-based phenotypic assay for the detection of drug resistant reverse transcriptase enzyme in the sample. The assay is useful for monitoring a patient's response to treatment with reverse transcriptase inhibitors so that, if resistance to a particular antiviral drug is detected, the treatment can be modified, even before actual symptoms of resistance or before clinically-relevant symptoms of resistance are observed, thereby keeping viral replication and the onset of opportunistic infection and disease at a minimum. The assay is also useful for isolating and identifying new antiviral drug-resistant retroviral strains, the emergence of known anti-viral drug resistant strains in patients, and for detecting the transmission of antiviral drug-resistant retroviral strains from patient to patient.

The phenotypic assay is based on the direct analysis of the susceptibility of reverse transcriptase in the sample to inhibition by a reverse transcriptase inhibitor drug by testing an active form of the drug that corresponds to a nucleoside triphosphate. Reverse transcriptase inhibitor drugs, and their active forms, include those such as, but not limited to, zidovudine (ZDV, also known as azidothymidine or AZT) and its active form AZT-triphosphate (AZT-TP), didanosine (ddI) and its active form dideoxyadenosine (ddA-TP), zalcitabine (ddC) and its active form ddC-triphosphate (ddC-TP), lamivudine (3TC) and its active form 3TC-TP, stavudine (d4T) and its active form d4T-TP, nevirapine (NVP), abacavir (ABC), delavirdine (DLV), loviride (LVD), efavirenz (EFV) and adefovir (bis-POM PMEA). Other forms of drugs can include those that are monophosphate or diphosphate forms, including those that can be converted to triphosphate forms in the treated patient.

The reverse transcriptase phenotype is based on the level of inhibition of reverse transcriptase by a fixed concentration of drug, and is determined after calculation of the ratio of units of reverse transcriptase activity/ml from a reverse transcriptase reaction made in the presence of drug to reference reactions in the absence of drug (×100). Drug concentrations resulting in 50% or 90% inhibition ($IC_{50}$ and $IC_{90}$) may also be determined by testing the reverse transcriptase with increasing concentrations of drug. The level of inhibition of reverse transcriptase by drug is used to define the susceptibility of the retrovirus to the drug.

The phenotypic assays to determine the presence of multiple nucleoside analog resistant (MNR) strains such as those where resistance is conferred by the Q151M mutation or the character of resistance of strains present are based on the level of inhibition of reverse transcriptase by a nucleoside analog reverse transcriptase inhibitor, such as AZT-TP. The assay uses enzymatic resistance of the reverse transcriptase, for example of HIV-1, to AZT-TP as a diagnostic marker of the Q151M-mediated MNR phenotype. Correspondingly, this assay can distinguish MNR viruses from either WT or conventional AZT-resistant viruses such as those containing T215Y/F mutations. MNR strains or the character of resistance of strains present are based on the level of inhibition of reverse transcriptase by a nucleoside analog reverse transcriptase inhibitor, such as AZT-triphosphate. In one aspect, these assays are conducted with a concentration or concentrations of AZT-TP that have been determined to result in levels of activity that differentiate between the strains that are wild-type, classical reverse transcriptase mutant strains or multiple nucleoside analog resistant mutant strains under those conditions of the assays. For example, in the presence of 1 µM AZT-triphosphate in the Amp-RT assay, the amount of DNA products that result from both wild-type and classical reverse transcriptase mutant strains are reduced by a significantly greater degree (at least by nearly 90%) relative to when there is no AZT-triphosphate included, whereas the level of DNA products from MNR strains are reduced by no more than approximately 30%. In particular aspects, determination that a relative amount of DNA product has been formed is established by comparison of the amount of DNA formed by the suspected strain or drug being tested and the amount of DNA product formed by a RT having known character or under conditions wherein the character of the RT can be established. The comparison of amounts of DNA formed allows one of skill in the art to ascertain the relative amount formed by the suspected strain being tested or the ability of the suspected strain to be inhibited by the drug present in a reaction. The relative presence of a DNA product can be defined as being 95% or greater, 90% or greater, 85% or greater, 80% or greater, 75% or greater, 70% or greater, 60% or greater, 50% or greater, 40% or greater, 30% or greater or 20% or greater than the amount of DNA formed when the RT is not contacted with the drug or if the RT is resistant and is contacted with the drug. The relative absence of a DNA product can be defined as being 5% or less, 10% or less, 15% or less, 20% or less, 30% or less, 40% or less, 50% or less, 60% or less or 70% or less of the amount of DNA product fonied when the RT is not contacted with the dnig or when the RT is contacted with the drug, but is resistant. As one of skill in the art will appreciate, variations of the above-outlined method can be made that are also encompassed within the scope of the invention. For example, it will be appreciated that the selection of conditions and the level of drug used can be used to optimize the amount of DNA product formed for resistant strains and non-resistant forms so as to allow ease and accuracy in determining whether a particular RT is resistant or non-resistant. Further, it is contemplated that other nulcleoside analog inhibitors of reverse transcriptase can be used instead of AZT-triphosphate, other levels of inhibition are taken as significant, other relative differences between the inhibition of DNA product formation can be considered significant and other concentrations of components or conditions can be utilized with the understanding that the changes made still result in a detectably different result when MNR strains are present or not or when the strains present in the sample have a different character or level of resistance.

For example, strains of HIV-1 can be characterized as being MNR mutants and as being distinct from wild-type or classical reverse transcriptase mutant strains. Such an assay could include: incubating a strain of HIV-1 with a reverse transcriptase inhibitor antiviral drug, an RNA template, and a first functionally complementary DNA primer, and detecting the presence or absence of a first DNA product, or a relative amount of a first DNA product, wherein the detection of the first DNA product or a certain relative amount of the first DNA product indicates that the strain of HIV-1 is an MNR mutant strain. In preferred embodiments: the RNA template is an RNA having no significant secondary structure, the RNA template is an RNA having less than 50% G-C content, and/or the RNA template includes sequence corresponding to sequence from a region of the encephalomyocarditis virus genome. As defined earlier, functionally complementary DNA primers are those that have adequate complementary to the RNA template to hybridize to the RNA template and to function as primers for reverse transcriptase.

In particular embodiments, the RNA template used can be an oligonucleotide having a sequence substantially the same as the sequence set forth in SEQ ID NO:4 or it can be an oligonucleotide having the sequence set forth in SEQ ID NO:4. The first functionally complementary DNA primer can be an oligonucleotide having the sequence set forth in SEQ ID NO:2 or any variant that hybridizes to the same region of SEQ ID NO:4 as SEQ ID NO:2 under conditions suitable for the oligonucleotide to function as a primer. The reverse transcriptase inhibitor used can be AZT-triphosphate.

As will be recognized by those of skill in the art, many methods can be used to detect the DNA product. For example, the DNA product can be detected by hybridization to a detectable hybridization probe, or by direct detection of the DNA product itself using methods and techniques known to those of skill in the art. If a detectable hybridization probe is used, the exact conditions and sequences for the hybridization probe and the design and construction of the probe can be varied in accordance with the teachings and knowledge of the art. For example, the hybridization probe can be an oligonucleotide having the sequence set forth in SEQ ID NO:3. As will be appreciate by those of skill in the art, as the assay of the invention can be accomplished so as to maximize the quantity of pertinent sequence of the DNA product, relative to any other closely related sequence, the hybridization probe need not necessarily be an exact complement to the site to which it binds so long as the binding is adequate to allow detection of the DNA product and the binding to other nucleic acids besides the DNA product is not so great as to either deplete the amount of hybridization probe available to bind the DNA product or so great as to cause false positive signals. Also, as will be appreciated, steps or processes that can separate or distinguish between complexes of the hybridization probe and the DNA product and complexes of the hybridization probe and any other factor can be used to diminish or eliminate false positive signals.

The method can further include incubating the retrovirus, RNA template and first functionally complementary DNA primer with a second functionally complementary DNA primer wherein the second functionally complementary DNA primer is extended during amplification to form a second DNA product. The second functionally complementary primer can include sequence corresponding to sequence from the encephalomyocarditis virus genome. An example of such a second functionally complementary DNA primer, for use with oligonucleotides having or containing the sequences of SEQ ID NOS:2-4, is an oligonucleotide having the sequence set forth in SEQ ID NO:1.

Similarly, a variation of the method can be used to identify the presence of retrovirus strains with mutations that confer multiple nucleoside analog resistance.

The terms "a", "an" and "the" as used herein are defined to mean "one or more" and include the plural unless the context is inappropriate.

The biological sample to be tested may be taken from an individual, such as a wound, blood, secretion, tissue, bone, muscle, cartilage, or skin sample or may be a laboratory research sample such as a cell culture supernatant, viral isolate or viral concentrate. The sample may be may be obtained from any biological source and is preferably taken from a human or animal capable of being infected with or harboring a retrovirus. For example, the sample may be a biological fluid, such as whole blood, blood serum, blood plasma, vaginal lavage, semen, urine, saliva, sputum, cerebrospinal fluid, lacrimal fluid, fermentation fluid, lymph fluid, tissue culture fluid, ascites fluid, synovial fluid, pleural fluid, and the like. The preferred biological sample is a biological fluid from which cells can be removed. The most preferred samples are blood plasma or serum. The sample is collected or obtained using methods well known to those skilled in the art.

The sample may be diluted, purified, concentrated, filtered, dissolved, suspended or otherwise manipulated prior to use in the assay. Preferably, a sample containing particulate matter is diluted, filtered, or both diluted and filtered prior to use. One feature of the present assay is that it is useful for the direct analysis of drug resistance from a biological body fluid sample such as blood serum or plasma, saliva, cerebrospinal fluid and similar body fluids. Therefore, such a sample need not be processed prior to being combined with the assay reagents, thereby facilitating sample analysis and minimizing the amount of labor, materials, time and expenses involved in performing the assay. The sample size for the biological fluid sample is preferably between approximately 0.5 µl and 1 ml, but is limited only by practical considerations.

The retrovirus present in the sample, or infecting the human or animal from which the sample is taken, is a virus characterized by the presence of reverse transcriptase, which transcribes the viral genomic RNA into a double-stranded DNA copy. Exemplary retroviruses for which a determination of drug resistance is sought include lentiviruses such as HIV-1 and HIV-2 and oncoviruses such as human T lymphocytic virus types I and II (HTLV-1 and HTLV-II). It will be understood by those skilled in the art that assays for retroviral drug resistance in species other than humans, such as nonhuman primates, cats, pigs, horses, and mice are included within the scope of the assay described herein.

The enzymatic activity of the reverse transcriptase enzyme of a retrovirus in the sample can be determined by measuring the DNA product produced when an RNA template and a first complementary DNA primer, from, for example, a suitable region of the encephalomyocarditis virus genome, are incubated with a biological sample containing reverse transcriptase in the presence one or more drugs to which resistance is being determined, or drug homologs. As a comparative control, the enzymatic activity of the reverse transcriptase enzyme is also determined in the absence of the reverse transcriptase inhibitor. A comparison of these results provides confirmation of drug resistance and an indication as to the extent of resistance.

The concentration of drug added to the assay depends on the drug employed and the concentration of drug normally administered to a patient. For example, the concentration of 3TC added to an assay for a determination of 3TC resistance is preferably between approximately 1 and 10 µM, most preferably approximately 5 µM. The preferred concentration of nevirapine used in the assay is between approximately 1 and 100 µM, most preferably approximately 50 µM. The preferred concentration of AZT-triphosphate is preferably between 0.1 and 50 µM. It will be understood that suitable concentrations for other reverse transcriptase inhibitors can be obtained from the art or can be calculated or experimentally determined using methods known to those skilled in the art. Optimization and selection of appropriate ranges of drug concentrations to use is contemplated herein and would be recognized by those of ordinary skill in the art to be conveyed by the teachings herein. Specifically, for each drug of interest selected, a range of concentrations can be used to determine the level of product formed when reverse transcriptase of known character or reverse transcriptase from species of known character is used. Selection of conditions wherein the difference in the level of DNA product formed when an RT of different character is used can be accomplished by one of skill in the art using the examples and disclosure included herein.

The term "suitable region" is defined herein as a region of RNA sequence that has the required characteristics of an RNA template for use in the assay as will be appreciated by those of skill in the art. A particular example of a suitable region is a region of the encephalomyocarditis virus RNA sequence having no significant secondary structure, less than 50% G-C content and to which complementary DNA primers can be generated which have Tm values within the range of reaction temperatures appropriate for the synthesis of a DNA strand, as described below. The RNA template can be of a length sufficient to produce a DNA product ranging in size from 100 to 500 base pairs in length, most preferably approximately 300 base pairs in length. The RNA template is most preferably the ribonucleotide of SEQ ID NO:4, which has the following sequence:

```
5' CAUUAGCCAU UUCAACCCAU GCGUUUGAGG AGAAGCGCUU     40

UCUGAUAACC GGUGGUCUCC CAUCAGGUUG UGCAGCGACC     80

UCAAUGCUAA ACACUAUAAU GAAUAAUAUA AUAAUUAGGG    120

CGGGUUUGUA UCUCACGUAU AAAAAUUUUG AAUUUGAUGA    160

UGUGAAGGUG UUGUCGUACG GAGAUGAUCU CCUUGUGGCC    200

ACAAAUUACC AAUUGGAUUU UGAUAAGGUG AGAGCAAGCC    240

UCGCAAAGAC AGGAUAUAAG AUAACUCCCG CUAACACAAC    280

UUCUACCUUU CCUCUUAAUU CGACGCUUGA AGACGUUGUC    320

UUCUUAAAAA GAAAGUUUAA GAAAGAGGGC CCUCUGUAUC    360

GGCCUGUCAU GAAC 3'
```

The incubation mixture is reacted or incubated under conditions whereby the RNA template and the DNA primer will anneal and a DNA strand will be synthesized as an extension from the DNA primer if the reverse transcriptase in the sample is resistant to and therefore not inhibited by the drug. This first DNA product can be amplified using a second complementary DNA primer corresponding to sequence from the encephalomyocarditis virus genome and suitable DNA amplification reagents and conditions. Either the first DNA product or the second DNA product, or both, can be detected in accordance with methods known to those skilled in the art. Examples include the hybridization of a detectable hybridization probe to a DNA product and detection of the hybridization. SEQ ID NO:3 is an example of a suitable hybridization probe as outlined in the examples. Detection of either the first or second DNA product, or both, indicates resistance to the drug employed in the assay.

As used herein, the term "complementary DNA primer" means an oligonucleotide which anneals to the RNA template in a particular orientation to allow for the synthesis of a nascent DNA strand in the presence of reverse transcriptase in the biological sample under the conditions described herein. Also as used herein, the "condition" under which a DNA strand is synthesized include the presence of nucleotides, cations and appropriate buffering agents in amounts and at temperatures such that the RNA template and the DNA primer will anneal and oligonucleotides will be incorporated into a synthesized DNA strand if reverse transcriptase is not inhibited by the reverse transcriptase inhibitor drug. Exemplary conditions are set forth in the examples below. The described conditions have been optimized from other known RT/cDNA synthesis protocols. It is generally known that other conditions can be established for optimization of a particular reverse transcriptase reaction on the basis of protocols well known to one of ordinary skill in the art. The DNA primer can be the reverse primer of a primer pair to be used in a subsequent amplification, such as, for example, the oligonucleotide of SEQ ID NO:2 (EMCR2), which has the following sequence: 5' GTTCATGACA GGCCGATACA GAGG 3'

Preferably, the second DNA primer consists of the oligonucleotide of SEQ ID NO:1, which has the following sequence: 5' CATTAGCCAT TTCAACCCAT 3'

The synthesized strand can be amplified by any of the amplification protocols known in the art now or in the future, including but not limited to the polymerase chain reaction (PCR), the ligation amplification reaction (LAR), the ligase-based amplification system (LAS), the self-sustained sequence replication (3SR) system, the transcription-based amplification system (TAS), and the Qβ replicase amplification method. The preferred amplification method is PCR.

For amplification by PCR, the conditions for amplification can include 30-40 cycles (preferably 35 cycles) of heating the synthesized DNA and primer pair to 93° to 97° C. (preferably 95° C.) for 30 to 90 seconds (preferably one minute), at 53° to 57° C. (preferably 55° C.) for 30 to 90 seconds (preferably one minute), and at 70° to 74° C. (preferably 72 C) for 30 to 90 seconds (preferably one minute). As will be recognized by those of skill in the art, the exact conditions to be used can be varied in accordance with the knowledge of those of skill in the art.

Similarly, while the amplified synthesized DNA is preferably detected by an enzyme linked immunosorbent assay (ELISA). Many other methods can be used and are fully comprehended by the present disclosure. In particular, methods that rely upon the identification of the presence of a sequence by hybridization or by sequence specific interactions can be used. These include, but are not limited to, ELISA based techniques, Southern blot hybridization, and energy transfer techniques such as FRET.

As used herein, the term "primer pair" refers to two primers, one having a forward designation and the other having a reverse designation relative to their, respective orientations on a double-stranded DNA molecule which consists of a sense and antisense sequence, such that under the amplification conditions described herein, the forward primer anneals to and primes amplification of the sense sequence and the reverse primer anneals to and primes amplification of the antisense sequence. Primers can be selected for use in the amplification reaction on the basis of having less than 50% G-C content, having minimal complementarity with other primers in the reaction (to minimize the formation of primer dimers) and having Tm values with the range of reaction temperatures appropriate for the amplification method, preferably PCR. In addition, primers can be selected to anneal with specific regions of the RNA template such that the resulting DNA amplification product ranges in size from 100 to 500 base pairs in length and most preferably around 300 base pairs in length. For example, in the conditions described above, the primer pair can consist of the oligonucleotide of SEQ ID NO:1 (EMCF1) as the forward primer and the oligonucleotide of SEQ ID NO:2 (EMCR2) as the reverse primer.

As used herein, the terms "detecting" or "detection" of the amplified DNA refers to qualitatively or quantitatively determining the presence of the amplified DNA strand, which is only synthesized if reverse transcriptase is resistant to the reverse transcriptase inhibitor drug added to the assay mixture. The amplification of the synthesized DNA can be detected by any method for the detection of DNA known in the art. For example, detection of the amplified DNA can be by Southern blot hybridization assay, by visualization of DNA amplification products of specific molecular weight on ethidium bromide stained agarose gels, by measurement of the incorporation of radio-labeled nucleotides into the synthesized DNA strand by autoradiography or scintillation measurement, by ELISA modified for the capture of a detectable moiety bound to the amplified DNA, or any other detection method known to one of ordinary skill in the art. The preferred detection method is by hybridization of the amplified DNA to an internal specific oligoprobe using techniques such as ELISA. Southern blot hybridization or similar method, most preferably using the specific hybridization probe of SEQ ID NO:3, which has the following sequence: 5' TGCTCTCACC TTATCAAAAT CCAAT 3'

Additionally provided is a kit for determining reverse transcriptase inhibitor drug resistance in a biological sample. The kit contains a suitable region of the encephalomyocarditis virus genome as an RNA template, a first complementary DNA primer for reverse transcriptase, and a second complementary DNA primer for amplification via the polymerase chain reaction, whereby each component is provided in separate containers or any combination of the components is provided in a single container. The kit may optionally contain a sample of the drug to which resistance is being determined, a hybridization probe for detection of the amplified DNA product, an apparatus for conducting the assay, an apparatus for assay detection, one or more containers for obtaining and storing the sample prior to and during analysis, and suitable buffers and other reagents to facilitate nucleic acid hybridization, synthesis, amplification and detection.

Figure 1B:
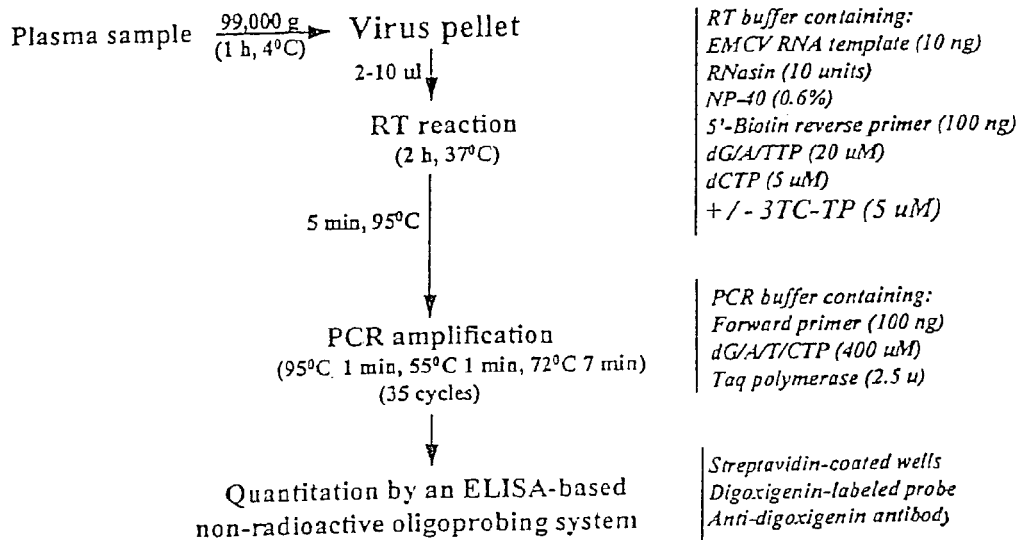
FIG. 1B is a flow chart depicting a protocol for the rapid analysis of HIV-1 resistance to 3TC using the reverse transcriptase-based phenotypic assay.

A preferred embodiment of the assay method described herein for the detection of 3TC-TP, ddC-TP, ddA-TP (active form of ddI), AZT-TP, ABC-TP, Tenofovir-TP, NVP-TP and other nucleoside/nucleotide analog resistant HIV-1 reverse transcriptase activity in plasma is shown as a flow chart in FIG. 1A. The protocol for the assay is set forth in FIG. 1B. The preferred assay, also referred to as the Amp-RT assay, is also described in copending application Ser. No. 08/763,762, now issued U.S. Pat. No. 5,849,494, which is incorporated by reference herein.

Preferred embodiments of the assay method described herein for the detection of MNR strains or mutants of HIV-1 in samples are described in Example 3 and elsewhere in the specification. These embodiments allow the detection of MNR strains, distinguishing MNR strains from classically resistant or wild-type strains and of relative quantification of MNR strains among samples.

In another preferred embodiment of the invention, a method to distinguish between retrovirus strains bearing classical reverse transcriptase mutations and those that are MNR is provided. The method includes identifying nucleoside analog resistant strains and testing the strains using a method that includes; incubating a sample containing a resistant retrovirus strain with a reverse transcriptase inhibitor drug wherein the drug is a nucleoside analog, an RNA template, and a first functionally complementary DNA primer and detecting the presence or absence of a first DNA product, wherein the absence of the first DNA product indicates the absence of a retrovirus strain having multiple nucleoside analog resistance and wherein this absence with the known resistance of nucleoside analog resistance of the tested strain indicates that the retrovirus strain has classical reverse transcriptase mutations.

The RNA template can be an RNA template having minimal secondary content under conditions similar or identical to those used during the assay where extension of the first primer occurs. Minimal secondary structure as described herein includes any level of structure wherein the structure does not appreciably interfere with the rate of primer extension or does not diminish the synthesis of DNA product to such a level that addition of nucleoside analog inhibitors of the selected reverse transcriptase such that the resulting levels of product formed with or without the inhibitor are indistinguishable. Suitable examples of such RNA templates include RNA templates having characteristics selected from the group consisting of; less than 50% G-C content and little or no secondary structure. Preferably, the RNA template comprises sequence from an RNA virus. Preferably, the RNA template comprises sequence from an encephalomyocarditis virus. Preferred first and second DNA primers are functionally complementary primers as described. Preferably, the first and second DNA primers are complementary to regions in the RNA template and first DNA product, respectively. For instance, preferably, the RNA template consists of the ribonucleotide of SEQ ID NO:4; the first DNA primer consists of the oligonucleotide of SEQ ID NO:2; the second DNA primer consists of the oligonucleotide of SEQ ID NO:1; and PCR amplification is achieved by utilizing 30-40 cycles of heating the synthesized DNA and primer pair to 93° to 97° C. for 30 to 90 seconds, at 53° to 57° C. for 30 to 90 seconds, and at 70° to 74° C. for 30 to 90 seconds. The amplified synthesized DNA can be detected by hybridization to a detectable hybridization probe. The detectable hybridization probe can be an internal specific oligoprobe using an enzyme linked immunosorbent assay (ELISA), Southern blot hybridization methods, or similar methods. For example, the oligonucleotides and drugs as described in Examples 1-3 can be used. Nucleoside resistant strains, such as those only bearing a mutation at position 215 that confers nucleoside analog resistance, will not, when tested using AZT-triphosphate result in an amplified, detectable signal comparable to that obtained when MNR strains are tested. Indeed, the result obtained will be most similar to that obtained for wild-type strains. Correspondingly, use of the assay can be used to differentiate nucleoside analog resistant strains into those with classical mutations and those with MNR mutations. Further examples of templates and primers that can be adapted to the present assay using the teachings contained herein and teachings illustrating the design, selection and use of templates and primers can be found in U.S. Pat. No. 5,806,669; Pyra et al. *Proc. Natl. Acad. Sci. USA* 91: 1544-1548 (1994); Silver et al., *Nucl. Acids Res.* 21: 3593-3594 (1993); and Palmenberg et al., *Nucl. Acids Res.* 12: 2969-2985 (1984) each incorporated herein by reference for the teachings relating to templates and primers.

In contrast to culture-based phenotypic assays, the reverse transcriptase-based phenotypic assay described herein is a highly sensitive, rapid and simple method for the direct analysis of phenotypic resistance to reverse transcriptase inhibitor drugs, and therefore provides a feasible tool for clinical monitoring and management of drug resistance. The assay is useful for the determination of phenotypic resistance to both known and unknown genotypic mutations. This assay approach is expandable to analysis of resistance to a wide variety of reverse transcriptase inhibitor drugs, and may also be useful for surveillance of transmission of drug-resistant viruses.

EXAMPLE 1

Determination of Phenotypic Resistance to 3TC

This example describes the use of a rapid nonculture-based assay for the analysis of phenotypic resistance to 3TC in plasma HIV-1. The assay, referred to as the Amp-RT assay, was based on the direct analysis of the susceptibility of plasma HIV-1 reverse transcriptase to inhibition by 3TC-TP. The assay successfully detected phenotypic resistance to 3TC in plasma samples from 3TC-treated patients. Resistance to 3TC in HIV-1 reverse transcriptase carrying mutations associated with multi nucleoside analog resistance (MNR) was also identified.

Materials and Methods

The phenotypic assay used in this example was based on the analysis of the susceptibility of HIV-1 reverse transcriptase activity from plasma to inhibition by 3TC-TP. Susceptibility of plasma reverse transcriptase to 3TC-TP was determined based on the level of inhibition produced by 3TC-TP, and was measured by running quantitative assays in the presence and absence of 3TC-TP.

The assay detects reverse transcriptase activity by using a nonretroviral heteropolymeric RNA template derived from the encephalomyocarditis virus (EMCV) genome, and a complementary EMCV-specific DNA oligoprimer. The RT-generated EMCV cDNA is detected by PCR amplification and internal oligoprobing of the PCR product with an EMCV-specific probe.

For culture supernatant, 10 µl were directly used for the reverse transcriptase reaction. The analysis of phenotypic resistance in plasma samples was made in plasma-free virus pellets as described in the protocol set forth in FIG. 1B. A volume of 100 µl of EDTA plasma was clarified by centrifugation at 10,000 g for five minutes, and then ultracentrifuged at a fixed angle at 99,000 g for one hour at 4° C. The viral pellet was resuspended in 100 µl of reverse transcriptase buffer (50 mM Tris-HCl, 50 mM KCl, 10 mM $MgCl_2$), and aliquots of 2 to 10 µl were used for the analysis of phenotypic resistance.

For quantitation of reverse transcriptase levels, a standard curve was generated by using known reverse transcriptase units from a reference HIV-1 stock (Virology Quality Assurance Laboratory, Rush-Presbyterian-St. Luke's Medical Center, Chicago, Ill.). This virus stock was shown to have $0.96 \times 10^{-10}$ units of reverse transcriptase activity/virion. Quantitative detection of Amp-RT products was made by using an ELISA-based, nonradioactive, oligoprobing system with an internal EMCV-specific probe. The results of Amp-RT signals were expressed as units of reverse transcriptase activity per milliliter, and reflect the average of duplicate or triplicate results. Qualitative detection of Amp-RT products was made by Southern blot hybridization to a $^{32}$P-end-labeled EMCP1 probe.

Phenotypic resistance of HIV-1 to 3TC was measured by the Amp-RT assay. Amp-RT detects reverse transcriptase activity by using a heterologous RNA template derived from the encephalomyocarditis virus (EMCV), a complementary DNA oligoprimer, and PCR amplification of reverse transcriptase-generated EMCV cDNA. For the phenotypic analysis of 3TC resistance, 10 µl of culture supernatant or virus pellets from 2 to 10 µl of plasma were applied in duplicate to a reverse transcriptase buffer containing 10 ng of EMCV RNA template, 10 units of RNasin, 0.6% NP-40, 100 ng of the 5'-biotin-labeled EMCR2 antisense primer, 1 mM EGTA, 2 mM dithiothreitol, 50 mM Tris-HCl, 50 mM KCl and 10 nM $MgCl_2$, 20 µM of dATP, dGTP and dTTP, 5 µM of dCTP. To determine the susceptibility of the reverse transcriptase to 3TC-TP, an additional Amp-RT reaction was made in the presence of 3TC-TP, with concentrations of 3TC-TP ranging from 0.1 to 10 µM. The reactions were incubated at 37° C. for two hours and heated at 95° C. for five minutes to destroy reverse transcriptase activity. PCR amplification of reverse transcriptase products was made as follows after the addition of 200 µM of each dNTP. A volume of 50 µl of PCR buffer containing 2.5 units of Taq polymerase, 100 ng of the sense primer EMCF1, and 200 µM of each dNTP was added to the reverse transcriptase mixture. The reaction was cycled 35 times at 95° C. for one minute, 55° C. for one minute, and 72° C. for one minute.

As described above, for quantitation of reverse transcriptase levels, a standard curve was generated by using known virion numbers of the reference HIV-1 virus stock. The method described by Garcia Lerma et al., *J. Infect. Dis.* 177: 1221-1229 (1998) was used for characterization of the reverse transcriptase activity in the reference virus as well as the quantitation of Amp-RT products by an ELISA-based non-radioactive oligoprobing system. The samples were considered as positive when duplicate test results were positive. Qualitative detection of Amp-RT products was made by an ELISA-based non-radioactive oligoprobing system as described in FIG. 1B and by Heneine et al., *J. Infect. Dis.* 171: 1210-1216 (1995).

Susceptibility of HIV-1 reverse transcriptase to 3TC-TP was determined from the level of inhibition of reverse transcriptase activity by 3TC-TP. The percentage of inhibition was calculated by using the ratio of reverse transcriptase level obtained in Amp-RT reactions containing 3TC-TP to that seen in Amp-RT reactions made in the absence of 3TC-TP (×100). Drug concentrations resulting in 50% and 90% inhibition ($IC_{50}$ and $IC_{90}$) were also determined by testing reverse transcriptase in the presence of several 3TC-TP concentrations.

Detection of 3TC-resistance Mutations

Genotypic resistance to 3TC was analyzed by sequencing and/or by the genotyping HIV-1 Line probe assay (LiPA) to detect mutations at codon 184. This assay is based on reverse hybridization of a biotinylated PCR fragment with short, immobilized oligonucleotides as described by Stuyver et al., *Antimicrob. Agents Chemother.* 41: 284-291 (1997). A region of the HIV-1 reverse transcriptase comprising amino acid 19 to 233 was sequenced in selected samples.

Study Population

A total of 30 EDTA-plasma samples from 15 HIV-1-infected patients from the Veteran Administration Medical Center, Decatur, Ga., were studied. The samples were collected from patients before and during anti-retroviral therapy with 3TC. The Amp-RT-based phenotypic assay was done under code with respect to date of serial bleed and reverse transcriptase genotype. One plasma specimen from a blood donor who tested antibody negative for HIV-1/2, HTLV-I/II was used as an assay negative control.

Viruses and 3TC-5'-triphosphate (3TC-TP)

For assay development and validation, HIV-1 molecular infectious clones (MIC) xxBRUpitt and M184Vpitt were used as wild type (WT) and 3TC-resistant (M184V mutation) HIV-1 reference viruses, respectively. Other reference viruses (controls) included M184V/Y181CEU, Y181CEU, and HIV-1$_{RTMC}$/MT-2, representing 3TC and nevirapine-resistant (M184V/Y181C), nevirapine-resistant (Y181C), and AZT-resistant (D67N/K70R/T215F/K219Q) HIV-1 respectively as described by Larder et al., *Science* 246: 1155-1158 (1989). Wild type HIV-1$_{SUM9}$, and multiple dideoxy nucleoside-resistant HIV-1$_{SUM8}$ (Q151M mutation), HIV-1$_{SUM12}$ (F77L/F116Y/Q151M) and HIV-1$_{SUM13}$ (A62V/V75I/F77L/F116Y/Q151M) MICs were provided by Dr. Mitsuya as described by Shirasaka et al., *Proc. Natl. Acad. Sci. USA* 92: 2398-2402 (1995). The synthesis and preparation of 3TC-TP were carried out as described by Schinazi et al., *Antimicrob. Agents Chemother.* 36: 2423-2431 (1992). The crude 3TC-5-TP was purified by FPLC using a HiLoad 26/10Q Sepharose Fast Flow™ Pharmacia chromatography column (Pharmacia, Piscataway, N.J.) and gradient of TEAE buffer (pH 7.0). The compound was characterized by UV spectroscopy, proton and phosphorous NMR, mass spectroscopy and HPLC. The concentration of 3TC-TP resulting in 50% inhibition of incorporation of 3HdCTP into a (rI)n-dC12-18 template primer by recombinant p66/p51 HIV-1 reverse transcriptase (Biotechnology General, Rehovot, Israel) was 1.3 µM as determined by decrease in the formation of acid insoluble product compared to untreated control.

Results

Amp-RT Testing Conditions that Differentiates between Wild Type and 3TC-resistant HIV-1

Inhibition of reverse transcriptase by 3TC-TP results from the ability of 3TC-TP to act as a competitive inhibitor for 2'-deoxycytidine-5'-triphosphate (dCTP) and chain terminator as described by Arts and Wainberg, *Antimicrob. Agents Chemother.* 40: 527-540 (1996). To determine the optimal ratio of 3TC-TP and dCTP needed to inhibit wild type HIV-1 reverse transcriptase, but not 3TC-resistant reverse transcriptase, reverse transcriptase were tested from a wild type (xxBRUpitt) and a 3TC-resistant (M184Vpitt) HIV-1 in the presence of increasing concentrations of 3TC-TP (from 0.1 to 10 µM) and a fixed concentration of dCTP (5 µM). The 5 µM dCTP was the lowest concentration found that did not compromise the sensitivity of the Amp-RT assay.

Figure 2A:
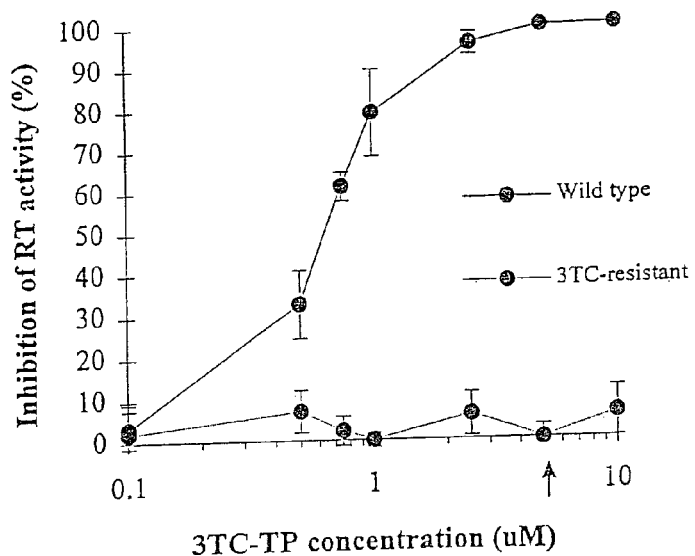
FIG. 2A is a graph showing the concentration of 3TC-triphosphate (3TC-TP) versus inhibition of reverse transcriptase activity in wild type ($xxBRU_{pitt}$) and 3TC-resistant ($M184V_{pitt}$) HIV-1. The arrow indicates the 3TC-TP concentration that differentiates between wild type and 3TC-resistant RT based on the level of RT inhibition.
Figure 2B:
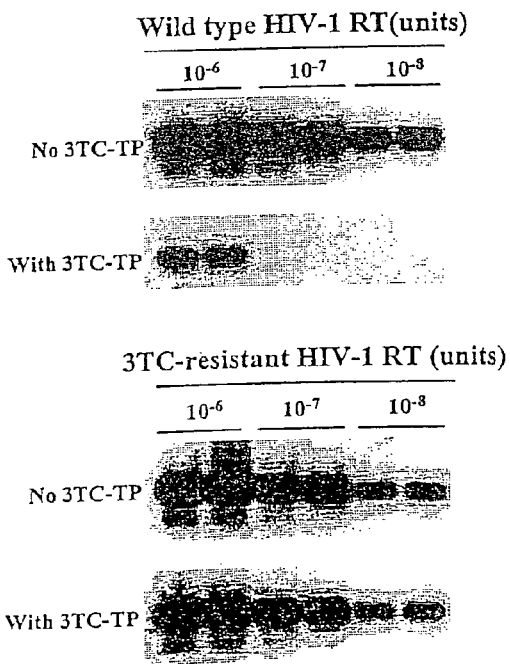
FIG. 2B is a representation of electrophoretic gels showing ten-fold serial dilutions of both wild type ($xxBRU_{pitt}$) and 3TC-resistant ($M184V_{pitt}$) HIV-1, tested in the presence and absence of 3TC-TP. A concentration of 5 µM 3TC-TP distinguishes between wild type and 3TC-resistant RT within a wide range of RT levels.

FIGS. 2A and 2B illustrate the inhibition seen with $10^{-7}$ units of reverse transcriptase activity, and shows that complete inhibition of the reverse transcriptase from the wild type, but not from the 3TC-resistant virus, was accomplished at 5 µM of 3TC-TP. This concentration of 3TC-TP was able to inhibit completely $10^{-7}$ and $10^{-8}$ units of reverse transcriptase activity from the wild type HIV-1 the equivalent to $10^5$ and $10^4$ HIV-1 particles/ml of the reference virus, respectively as shown in FIG. 2. With a higher input of reverse transcriptase ($10^{-6}$ units of reverse transcriptase activity; the equivalent to $10^6$ HIV-1 particles/ml of the reference virus), these conditions did not result in complete inhibition. The residual reverse transcriptase activity in the Amp-RT reaction containing 3TC-TP was found to be 0.4% of the Anmp-RT signal firom the control reaction that had no 3TC-TP. This reduction in reverse transcriptase signal is equivalent to a 2.35 $\log_{10}$ drop in Amp-RT virus load. No significant inhibition was seen in the 3TC-resistant HIV-1 tested at either high or low input of reverse transcriptase, demonstrating the ability of the assay to distinguish between wild type and 3TC-resistant reverse transcriptase within a wide range of reverse transcriptase levels. Based on these results, Amp-RT conditions containing 5 µM 3TC-TP as a primary screening assay for 3TC resistance was used in all testing unless otherwise indicated.

Figure 3:
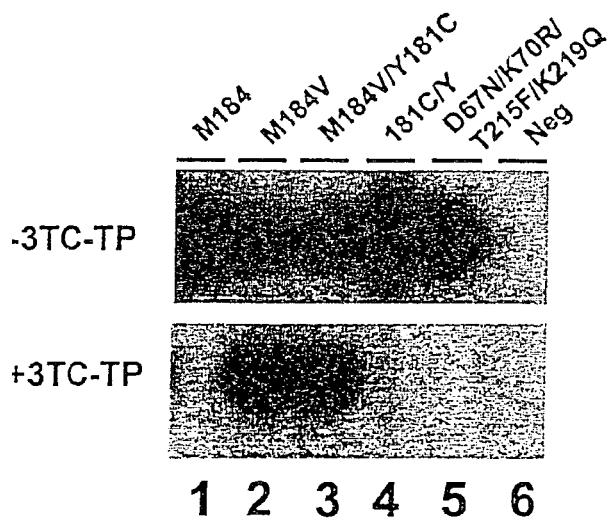
FIG. 3 is a representation of electrophoretic gels showing inhibition by 3TC-TP of HIV-1 having 3TC-, nevirapine- or AZT-resistance mutations. Lane 1 is wild type ($xxBRU_{pitt}$) HIV-1; lane 2 is 3TC-resistant ($M184V_{pitt}$) HIV-1; lane 3 is 3TC/nevirapine-resistant ($M184V/Y181C_{EU}$)HIV-1; lane 4 is nevirapine-resistant ($181C/Y_{EU}$) HIV-1; lane 5 is AZT-resistant (HIV-$1_{RTMC}$/MY-2) HIV-1; lane 6 is the negative control.

To demonstrate that the Amp-RT-based phenotypic assay was specific for 3TC resistance, several HIV-1 reference viruses well-characterized phenotypic resistance to nucleoside and non-nucleoside analogs were tested. FIG. 3 shows that resistance to 3TC was only seen in reverse transcriptases carrying the M184V mutation. As expected, HIV-1 reverse transcriptases carrying AZT (D67N, K70R, T215F, K219Q) or nevirapine (Y181C) resistance mutations were all found to be susceptible to 3TC-TP. These results confirm that the assay was specific for viruses with phenotypic resistance to 3TC, and indicate that the presence of other mutations associated with AZT and nevirapine resistance does not affect the inhibition of reverse transcriptase activity by 3TC-TP.

Assay Detection Threshold for Phenotypic Resistance to 3TC

Figure 4:
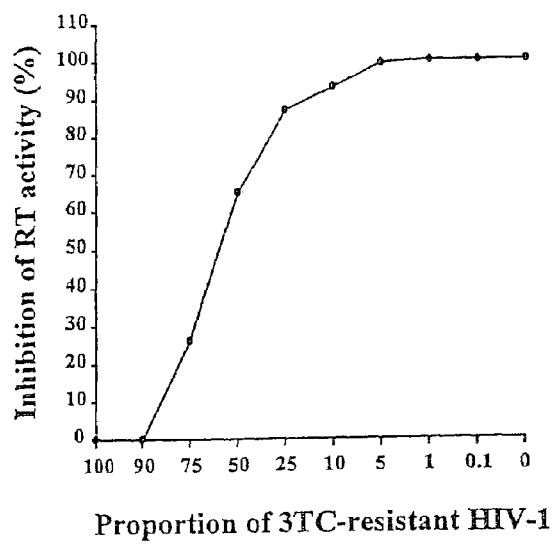
FIG. 4 is a graph showing the proportion of 3TC-resistant ($M184V_{pitt}$) HIV-1 in a background of wild type ($xxBRU_{pitt}$) HIV-1 versus inhibition of RT activity by 3TC-TP (5 µM).

The assay detection threshold for 3TC resistance was tested by mixing the wild type (xxBRUpitt) and 3TC-resistant (M184Vpitt) MIC at different proportions and testing for evidence of 3TC resistance. The reference viruses were adjusted to similar levels of reverse transcriptase activity before virus mixtures were prepared. The level of inhibition of reverse transcriptase activity by 3TC-TP observed in each mixture with the proportion of 3TC-resistant virus used was compared. FIG. 4 shows that the assay detection threshold was found to be 10% of 3TC-resistant viruses in a background of wild type HIV-1. A good correlation between the proportion of viruses carrying the M184V mutation and the level of inhibition was also observed. For instance, in mixtures containing 25% or 75% of 3TC-resistant virus, the observed inhibition was 87% and 26%, respectively, which very likely represents the signals from the 3TC-resistant reverse transcliptase and, therefore suggests that only wild type reverse transcriptase activity was inlibited.

The same mixtures were used to compare the detection threshold of the Amp-RT-based phenotypic assay with the genotypic detection threshold for viruses carrying the M184V mutation by the LiPA assay as shown in FIG. 4. The detection threshold of 3TC-resistant virus by the HIV-1 LiPA assay was 10%, indicating that both assays can reliably detect low levels of either genotypic or phenotypic resistance to 3TC. However, signal intensities in mixtures containing 50% wild type and 50% 3TC-resistant virus were not similar in the LiPA assay. This may be due to different levels of HIV-1 RNA in both reference viruses resulting from adjustment of virus by reverse transcriptase activity rather than by RNA levels or to different efficiencies in the hybridization of the wild type or 184V-specific probes.

Multi-drug Resistance Mutations Confer Phenotypic Resistance to 3TC

Mutations in codon 151 of the HIV-1 reverse transcriptase have been associated with resistance to several dideoxynucleoside analogs including AZT, ddC, ddI and d4T. HIV-1 containing mutations associated with MD resistance to several dideoxynucleoside analogs were analyzed to determine if mutations other than 184V confer resistance to 3TC. The Amp-RT $IC_{50}$ and $IC_{90}$ values for 3TC of viruses containing one (Q151M; HIV-1SUM 8), three (F77L/F116Y/Q151M; HIV-SUM 12), and all five mutations associated with MD resistance (A62V/V751/F77L/F116Y/Q151M; HIV-1SUM 13) were determined. Control wild type HIV-1 reverse transcriptases were also tested.

The reverse transcriptase from HIV-1 carrying the Q151M mutation had a slightly reduced susceptibility to 3TC, with $IC_{50}$ and $IC_{90}$ values approximately two-fold higher than those of reverse transcriptase reference viruses. However, the presence of additional multidrug (MD) resistance mutations resulted in higher levels of resistance to 3TC, with an increase in $IC_{50}$ values of six- and eight-fold for virus with three or all five MD resistance mutations, respectively, compared to wild type virus which had similar $IC_{50}$ and $IC_{90}$ values for 3TC-TP. These results suggest that these multidrug resistance mutations in HIV-1 reverse transcriptase confer phenotypic resistance to 3TC.

Analysis of Phenotypic Resistance to 3TC in Plasma HIV-1 RT and Correlation with Mutations at Codon 184

The performance of the Amp-RT-based phenotypic assay with plasma samples was evaluated by testing 30 specimens collected from 15 HIV-1-infected patients before and during treatment with 3TC. The results are shown in Tables 1 and 2 below. All pretreatment samples (n=12) had wild type phenotypes, with reverse transcriptase inhibition values of greater than 95%. The observed inhibition in these samples ranged from 95.9% to 100% (mean=98.7%+1.8%; median=99.8%). Of these samples, 11 had wild type genotypes at codon 184 and one had a mixture of wild type and M184I (sample 7A). Mutations at codon 69, which is associated with resistance to ddC, were observed in samples from the two individuals who had lower susceptibility to 3TC-TP (samples 13A and 15A; reverse transcriptase inhibition values of 95.9% and 95.5%, respectively). The T69D mutation has been recently shown to confer low cross-resistance to 3TC (12-fold), and therefore, may be responsible for the decreased susceptibility to 3TC observed in these samples with the Amp-RT assay.

Figure 5:
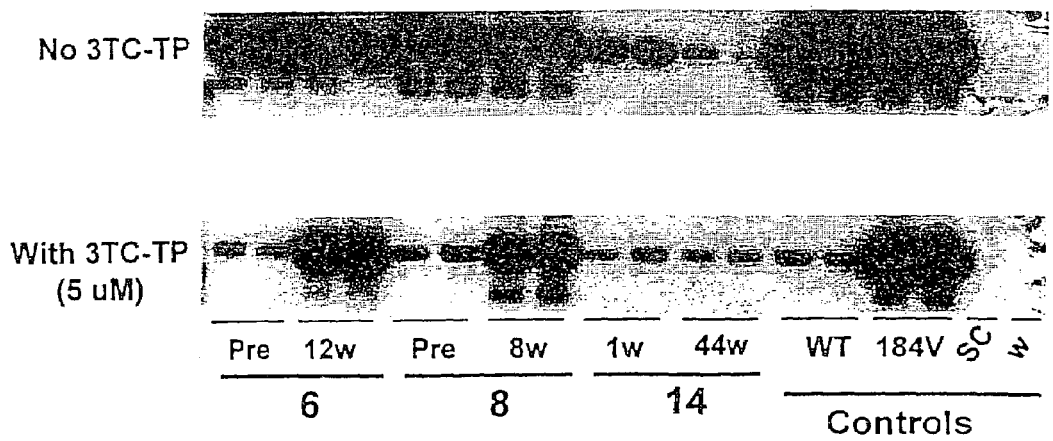
FIG. 5 is a schematic representation of electrophoretic gels showing inhibition by 3TC-TP of HIV-1 RT from plasma of three HIV-1-infected patients before and during therapy with AZT plus 3TC. Lane SC is HIV-1/2, HTLV I/II seronegative control. Lane W is water control.

In contrast, values of reverse transcriptase inhibition of less than 95% were only seen in samples obtained from patients after 1 to 60 weeks of antiretroviral therapy with 3TC (n=18). Of these samples, 12 had the M184V mutation, four had mixtures of wild type and M184V genotypes, and two (samples 10A and 14A) had only wild type genotypes. The mean inhibition in the samples with evidence of 184V only was 30.8% (median=24.9%), reflecting the high level of resistance to 3TC. The mean inhibition in samples with mixtures of wild type and resistant genotypes was 49.3% (median=52.4%), indicating lower levels of resistance, which was expected since these samples have higher proportions of wild type reverse transcriptase. The lower level of resistance to 3TC observed in post-therapy samples was seen in specimens collected after one and four weeks of therapy (samples 14A and 10A; reverse transcriptase inhibition values of 94.7% and 87.8%, respectively). Both samples had wild type genotype at codon 184. However, sample 14A had a T69D mutation that may explain the borderline susceptibility to 3TC. The absence of detectable 184V mutation in sample 10A may represent an earlier detection of phenotypic resistance, or may be due to the inability of the sequencing and LiPA assay to detect a low proportion of 3TC-resistant viruses. Both patients had high levels of 3TC resistance in samples obtained after 12 and 44 weeks of 3TC treatment (Table 1). FIG. 5 illustrates representative results for plasma from three patients, and shows the presence of phenotypic differences between specimens collected before and during antiretroviral therapy with 3TC.

Conclusion

The efficacy of antiretroviral therapy with reverse transcriptase inhibitors such as 3TC is strongly limited by the emergence of drug resistant HIV-1 variants. The assay used in this example is a rapid nonculture-based assay for the analysis of phenotypic resistance to 3TC of plasma HIV-1 reverse transcriptase. The assay used a small volume of plasma, and the HIV-1 reverse transcriptase phenotype for 3TC was determined based on the level of reverse transcriptase inhibition by a single 3TC-TP concentration. Compared to standard culture-based phenotypic assays, this approach has several advantages. First, test results were obtained in one to two days, providing rapid information on resistance to 3TC that should be of clinical relevance to treatment decisions and patient management. Second, testing is directly made on reverse transcriptase from plasma and, therefore, unlike culture-based methods, the assay does not select for particular viral isolates. Third, the assay has a low detection threshold for 3TC-resistant reverse transcriptase and may be useful for the early detection of 3TC resistance.

The data generated in this example demonstrate that the assay can be used to successfully monitor for resistance to 3TC mediated by mutations at codon 184Decreased reverse transcriptase inhibition by 3TC-TP occurred in samples obtained from persons after treatment with 3TC, and coincided with the emergence of resistant genotypes. In addition to providing phenotypic information on resistance to 3TC, the Amp-RT reaction done without 3TC-TP provided information on the reverse transcriptase-based plasma virus and, therefore, can be used to simultaneously monitor the virologic response to treatment with 3TC.

The assay was designed for rapid evaluation of resistance to 3TC and included testing with an optimal concentration of 3TC-TP. Using this assay format, an interesting association was found between mutations at codon 69 and borderline susceptibility to 3TC-TP, suggesting that this mutation may confer some level of resistance to 3TC. To further clarify the role of the observed borderline susceptibility in samples with mutations at codon 69 or others, the assay format can be modified to include testing with several concentrations of 3TC-TP to better quantitate the level of resistance to 3TC. In addition to clinical monitoring of 3TC resistance, the assay may also be used as a rapid method for surveillance of transmission of 3TC resistance among persons with newly diagnosed HIV-1 infections and for detection of resistance to 3TC in 3TC-naive HIV-1-infected patients.

TABLE 1

| Sample | Weeks | Treatment | RT activity (units/ml) No 3TC-TP | With 3TC-TP (5 uM) | Inhibition of RT(%) | Mutations Codon 184 | Others |
|---|---|---|---|---|---|---|---|
| $1_B$ | Pre | AZT/ddC | $1.7 \times 10^{-9}$ | n.d | 100 | M184 | — |
| $1_E$ | 12 | AZT/3TC | $2.1 \times 10^{-6}$ | $5.1 \times 10^{-7}$ | 75.6 | V/M184 | L41; Y215 |
| $1_F$ | 18 | AZT/3TC | $1.3 \times 10^{-7}$ | $3.3 \times 10^{-8}$ | 75.9 | V184 | — |
| $2_B$ | Pre | AZT/ddC | $2.2 \times 10^{-6}$ | $6.3 \times 10^{-9}$ | 99.7 | M184 | — |
| $2_F$ | 12 | AZT/3TC | $1.5 \times 10^{-6}$ | $4.7 \times 10^{-7}$ | 68 | V184 | — |
| $3_B$ | Pre | AZT | $1.8 \times 10^{-6}$ | $1.7 \times 10^{-8}$ | 99.4 | M184 | — |
| $3_F$ | 12 | AZT/3TC | $1.6 \times 10^{-8}$ | $1.2 \times 10^{-9}$ | 92.3 | M/V184 | — |
| $3_G$ | 21 | AZT/3TC | $5.1 \times 10^{-9}$ | $1.0 \times 10^{-8}$ | 0 | V184 | — |
| $4_A$ | Pre | AZT | $1.6 \times 10^{-7}$ | $1.2 \times 10^{-10}$ | 99.9 | M184 | R70 |
| $4_B$ | 12 | AZT/3TC | n.d. | n.d. | — | V184 | R70 |
| $5_A$ | Pre | AZT | $1.2 \times 10^{-8}$ | n.d. | 100 | M184 | Y215 |
| $5_B$ | 4 | AZT/3TC | n.d. | n.d. | — | M/V184 | Y215 |
| $5_C$ | 10 | AZT/3TC | n.d. | n.d. | — | V184 | Y215 |
| $6_A$ | Pre | None | $7.7 \times 10^{-5}$ | $3.6 \times 10^{-8}$ | 99.9 | M184 | — |
| $6_B$ | 12 | AZT/3TC | $2.3 \times 10^{-5}$ | $1.5 \times 10^{-5}$ | 34.7 | V184 | — |
| $7_A$ | Pre | None | $1.2 \times 10^{-8}$ | n.d. | 100 | M/I184 | — |
| $7_C$ | 28 | AZT/3TC | n.d. | n.d. | — | V184 | — |
| $8_A$ | Pre | AZT | $4.4 \times 10^{-5}$ | $5.7 \times 10^{-8}$ | 99.9 | M184 | L41; Y215 |
| $8_B$ | 8 | AZT/3TC | $5.0 \times 10^{-5}$ | $4.3 \times 10^{-5}$ | 15 | V184 | L41; Y215 |
| $9_A$ | Pre | d4T | $2.9 \times 10^{-6}$ | $6.3 \times 10^{-8}$ | 97.8 | M184 | L41; Y215 |
| $9_F$ | 12 | AZT/3TC | $2.1 \times 10^{-6}$ | $1.1 \times 10^{-6}$ | 47 | V184 | L41; Y215 |
| $10_A$ | 4 | AZT/3TC | $8.9 \times 10^{-5}$ | $9.1 \times 10^{-6}$ | 87.8 | M184 | Y215? |
| $10_C$ | 12 | AZT/3TC | $1.9 \times 10^{-7}$ | $1.9 \times 10^{-7}$ | 0 | M/V184 | — |
| $10_G$ | 52 | AZT/3TC | $2.6 \times 10^{-5}$ | $3.5 \times 10^{-5}$ | 0 | V184 | L41; Y215 |
| $11_A$ | 12 | AZT/3TC | $1.9 \times 10^{-7}$ | $1.3 \times 10^{-7}$ | 29.1 | V/M184 | R70 |
| $11_C$ | 36 | AZT/3TC | $1.7 \times 10^{-7}$ | $7.0 \times 10^{-8}$ | 58.5 | V184 | R70 |
| $12_A$ | Pre | AZT | $2.5 \times 10^{-5}$ | $9.2 \times 10^{-7}$ | 96.3 | M184 | — |
| $12_E$ | 28 | AZT/3TC | $1.7 \times 10^{-6}$ | $5.1 \times 10^{-7}$ | 70 | V184 | R70; Y215 |
| $13_A$ | Pre | d4T | $1.5 \times 10^{-6}$ | $6.2 \times 10^{-8}$ | 95.9 | M184 | N69: R70 |
| $13_F$ | 60 | d4T/3TC/IND | $6.3 \times 10^{-5}$ | $7.4 \times 10^{-5}$ | 0 | V184 | L41; D/N69; R70 |

TABLE 1-continued

|  |  |  | RT activity (units/ml) |  | Inhibition | Mutations | |
|---|---|---|---|---|---|---|---|
|  |  |  |  | With 3TC-TP |  |  |  |
| Sample | Weeks | Treatment | No 3TC-TP | (5 uM) | of RT(%) | Codon 184 | Others |
| $14_A$ | 1 | AZT/3TC | $2.5 \times 10^{-7}$ | $1.3 \times 10^{-8}$ | 94.7 | M184 | L41; D69; R70; Y215 |
| $14_F$ | 44 | IND/3TC | $2.9 \times 10^{-9}$ | $5.1 \times 10^{-9}$ | 0 | V184 | D69; R70; Y215 |
| $15_A$ | Pre | AZT | $8.9 \times 10^{-5}$ | $4.0 \times 10^{-6}$ | 95.5 | M184 | D69 |
| $15_D$ | 40 | AZT/3TC/ IND | $1.6 \times 10^{-10}$ | $2.4 \times 10^{-10}$ | 0 | V184 | D69; Y215 | n.d. = not detected;
IND = indinavir
Previous treatments were: patient 9 was on AZT before first sample; patient 13 was on AZT/ddC before first sample; and patient 14 was on ddi for a period of time between first and second sample

TABLE 2

Amp-RT Detection of Phenotypic Resistance Correlates to Mutations at Codon 184

|  | Sensitive phenotype* | | | Resistant phenotype* | | |
|---|---|---|---|---|---|---|
|  | 184 wt | 184 wt-MT | 184 MT | 184 wt | 184 wt-MT | 184 MT |
| Pretreatment (n = 12) | 12 | 0 | 0 | 0 | 0 | 0 |
| 1-4 weeks (n = 2) | 0 | 0 | 0 | 2 | 0 | 0 |
| 4-12 weeks (n = 8) | 0 | 0 | 0 | 0 | 4* | 4 |
| >12 weeks (n = 8) | 0 | 0 | 0 | 0 | 0 | 8 |

*RT phenotype was determined based on the level of RT inhibition by 5 μM 3TC-TP.
wt-MT = a mixture of wild type and M184V

EXAMPLE 2

Determination of Phenotypic Resistance to Nevirapine

This example describes the use of a nonculture-based assay for the rapid analysis of phenotypic resistance to nevirapine in HIV-1 from plasma. The assay is based on the direct analysis of the susceptibility of plasma HIV-1 RT to inhibition by nevirapine. The assay used in this example was the PCR-based Amp-RT described in Example 1.

Materials and Methods

Susceptibility of plasma RT to nevirapine was determined based on the level of inhibition produced by the drug and was measured by running quantitative Amp-RT reactions in the presence and absence of nevirapine.

For culture supernatant, 10 μl were used directly in the Amp-RT assay. For plasma testing, a volume of 100 μl was clarified by centrifugation at 10,000 g for five minutes and then ultracentrifuged at a fixed angle at 99,000 g for 1 hour at 4° C. The viral pellet was resuspended in 100 μl of RT buffer (50 mM Tris-HCl, 50 mM KCl, 10 mM MgCl$_2$). Ten microliter aliquots of virus pellets were applied to an RT buffer containing 10 ng of EMCV RNA template, 10 units of RNasin, 0.6% NP-40, 100 ng of the 5'-biotin-labeled EMCR2 antisense primer, 1 nM EGTA, 2 mM dithiothreitol, 50 mM Tris-HCl, 50 mM KCl, 10 mM MgCl$_2$, and 400 uM of each dNTP. Reactions were incubated at 37° C. for 2 hours and then heated at 95° C. for five minutes to destroy RT activity. PCR amplification of RT products was preformed as previously described above in Example 1. The conditions for PCR were 35 cycles at 95° C. for one minute, 55° C. for one minute, and 72° C. for one minute.

For quantitation of RT levels, a standard curve was generated by using known RT units from a reference HIV-1 stock (Virology Quality Assurance Laboratory, Rush-Presbyterian-St. Luke's Medical Center, Chicago, Ill.). This virus stock, referred to as VQA, has been shown to have $0.96 \times 10^{-10}$ units of RT activity/virion. Quantitative detection of Amp-RT products was made by using an ELISA-based, nonradioactive, oligoprobing system with an internal EMCV-specific probe, as described by Garcia Lerna *J. Infect. Dis.* 177:1221-1229 (1998). All samples were tested within the linear range of the Amp-RT assay (from $10^{-6}$ to $10^{-10}$ units of RT activity). Samples which had levels of RT activity above the linear range of the assay, were further diluted in RT buffer and retested again. The minimum detectable level of HIV-1 RT activity by the Amp-RT in plasma is $10^{-10}$ units, the equivalent of 1 HIV-1 particle of the reference virus used for quantitation. The results of Amp-RT signals were expressed as units of RT activity per milliliter of plasma and reflect the average of duplicate results.

Detection of Phenotypic Resistance to Nevirapine by the Amp-RT Assay

To determine the susceptibility of plasma HIV-1 RT to nevirapine, Amp-RT reactions were run in the absence and presence of nevirapine. Percentage of inhibition was calculated by using the ratio of RT level seen in the presence of nevirapine to that seen in Amp-RT reactions made in the absence of nevirapine (×100). Nevirapine concentrations resulting in 50% and 90% inidbition (IC$_{50}$ and IC$_{90}$) of RT activity were measured by testing RTs in the presence of several concentrations of nevirapine and were determined by nonlinear regression as described by Shafer et al. *J. Infect. Dis.* 172:70-78 (1995).

Detection of Mutations at Codon 181 of the HIV-1 RT Gene in Plasma Samples

Levels of Y181C mutation in plasma HIV-1 RT were previously determined by differential hybridization as described by Havlir et al. *J. Virol.* 70:7894-7899 (1996). Briefly, viral RNA was amplified by RT-PCR using primers 5RT and 3RT. The resulting PCR product was added to streptavidine-coated wells and incubated at 50° C. for 30 minutes. After washing, a hybridization solution containing a specific probe for the Y181C mutation (MUT probe) was added and incubated for one hour at 45° C. To normalize for the amount of PCR product bound to each well, an additional probe to a highly conserved region of the HIV-1 RT (generic probe; GNR) was also used. Hybridization was measured by chemiluminiscence and results are expressed as MUT/GNR ratio. The threshold for considering detectable Y181C mutation has been defined by Havlir et al., 1996 as a MUT/GNR ratio of 0.03.

Quantitation of HIV-1 RNA Levels in Plasma

HIV-1 RNA levels in plasma samples were determined by an RT-PCR-based method (Roche Amplicor HIV Monitor Test), as specified by the manufacturer. The reported detection limit of the assay is 200 RNA copies/ml of plasma.

Study Population

A total of 30 plasma samples obtained from four HIV-1-infected patients (patients N12N06N07 and E01) were analyzed as described by Havlir et al. 1996. The four patients were enrolled in a double-blind clinical trial of nevirapine versus placebo at the University of California, San Diego. The daily dose of nevirapine was 200 mg for the first 14 days, and then 400 mg. A more detailed description of the study population was previously reported by Havlir et al. 1996.

Reference Viruses

For assay development and validation, HIV-1 isolates V818-5, S469-2/M3X165-11W786-6X82-5X403-4X165-6 and X267-1 were used. Susceptibility to nevirapine in these isolates was previously determined by a plaque-reduction assay as described by Havlir et al. 1996. Sequence analysis of the RT gene was done by standard methods as described by Mulder et al., *J. Clin. Microbiol.* 32: 292-300 (1994). Other reference viruses used included N119L6KL5M184V/Y181C$_{EU}$, M184V$_{pitt}$, HIV-1$_{RTMC}$/MT-2, and HIV-1$_{RTMDR1}$/MT-2, representing nevirapine-resistant Y181C (N119), K103N (L6KL5), nevirapine/3TC-resistant (181C/184V), 3TC-resistant (184V), AZT-resistant (67N/70R/215F/2419Q), and nevirapine/AZT/ddI-resistant (74V/41L/106A/215Y) HIV-1respectively as described by Richman et al., *Proc. Natl. Acad. Sci. USA* 88:11241-11245 (1991); Larder and Kemp, *Science* 246: 1155-1158 (1989); Larder et al., *Nature* 365:451-453 (1993); Schinazi et al., *Antimicrob. Agents Chemother.* 37: 875-881 (1993).

Results

Correlation Between Drug Susceptibility Results Derived by Amp-RT Analysis and Culture-based Assays The Amp-RT IC$_{50}$ values for nevirapine in eight HIV-1 reference isolates were compared with the IC$_{50}$ values obtained by a plaque-reduction assay. Table 3below, illustrates the level of RT inhibition seen by Amp-RT with $5 \times 10^{-8}$ units of input RT activity form each isolate (the equivalent of 500 HIV-1 particles of the VQA reference virus). The two WT isolates (isolates X267-1 and X165-6) had similar IC$_{50}$ in both assays, while isolates carrying mutations associated with nevirapine resistance (K103N, Y181C, G190A, or Y188L mutations) showed high level of phenotypic resistance (>100-fold increase in IC$_{50}$ compared to WT isolates). A strong correlation ($r^2$=0.95p <0.001) between IC$_{50}$ values determined by Amp-RT and by culture was observed, suggesting that RT-based drug susceptibility testing can be used to determine the HIV-1 phenotype for nevirapine.

TABLE 3

Specificity of Amp-RT Assay versus Culture

| HIV-1 isolate | Mutations | IC$_{50}$(µM)/fold* Culture | Amp-RT |
|---|---|---|---|
| X267-1 | — | 0.04 | 4 |
| X165-6 | — | 0.07/1.7 | 11/2.7 |
| X82-5 | K103N, Y181C | 4.6/115 | 491/123 |
| X403-4 | Y181C | 9/225 | 571/143 |
| W786-6 | K103N, Y181C | 20/400 | 2283/570 |
| X165-11 | G190A, Y181C | 22/550 | 1474/369 |
| S469-2/M3 | Y188L | 100/2500 | 2642/661 |
| V818-5 | G190A, Y181C | >100/>2500 | 9804/2451 |

*fold-resistance compared to isolate X267-1

Figure 6:
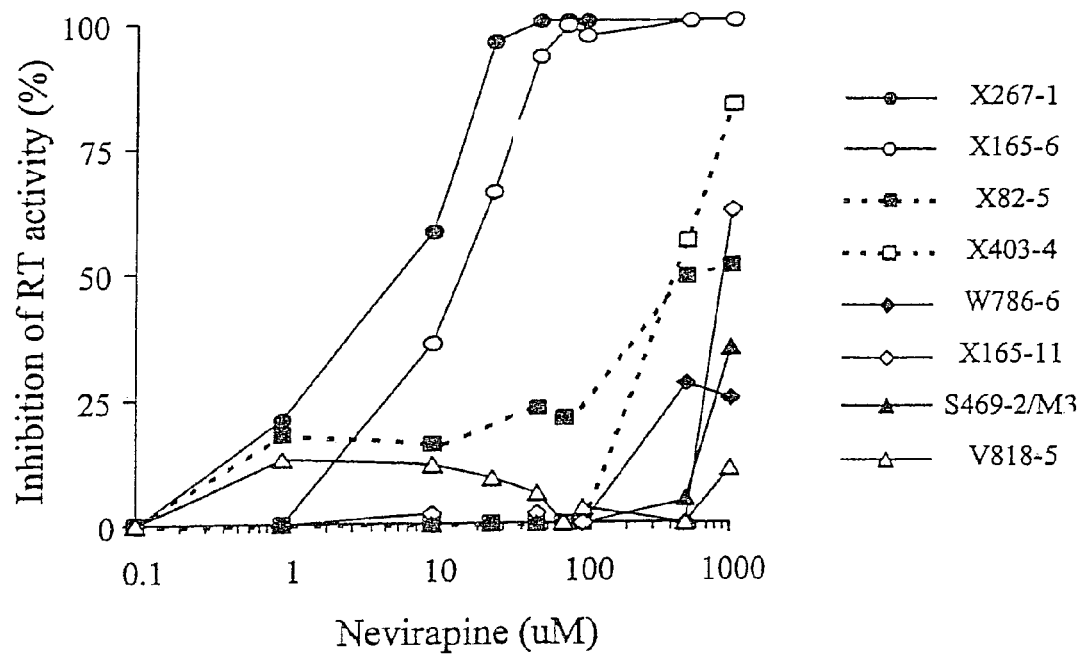
FIG. 6 is a graph of nevirapine concentration versus inhibition of reverse transcriptase activity for wild type and nevirapine-resistant reference isolates.

Detection of Nevirapine Resistance in a Single Amp-RT Reaction Containing 50 µM Nevirapine The analysis of the RT inhibition values by nevirapine in the wild type and nevirapine-resistant reference isolates demonstrated that a concentration of 50 µM nevirapine only inhibited the RT from the two wild type isolates (isolates X267-1 and X165-6), while little or no inhibition of RT activity was seen with the resistant isolates as shown in FIG. 6. These results suggest that a single Amp-RT reaction containing 50 µM nevirapine could be used for rapid screening of nevirapine resistance in plasma.

A concentration of 50 µM nevirapine was analyzed to determine whether this concentration could distinguish between wild type and nevirapine-resistant HIV-1 RT tested at different levels of input RT activity. As shown in Table 4, below, 50 µM nevirapine resulted in complete inhibition of approximately $7 \times 10^{-8}$ and $7 \times 10^{-9}$ units of RT activity from a nevirapine-sensitive HIV-1 isolate (isolate X267-1), which are equivalent to approximately 700 and 70 HIV-1 particles of the VQA reference virus, respectively. With a higher input of RT activity ($7 \times 10^{-7}$ units), these conditions resulted in 98.6% RT inhibition. In contrast, no significant inhibition was seen in the nevirapine-resistant HIV-1 RT from isolates X403-4 and W786-6 tested at either high or low input of RT. For example, when $8.3 \times 10^{-9}$ units of RT activity from isolate W786-6 were tested (the equivalent to 80 particles of the VQA reference virus), no significant inhibition by 50 µM nevirapine was observed as shown in Table 4. These results demonstrate the ability of this assay to distinguish between wild type and nevirapine-resistant RTs within a three-log$_{10}$ range of input RT.

TABLE 4

Effect of Input of RT Activity on RT Inhibition by 50 µM Nevirapine in the Amp-RT Assay

| | Units of RT activity* | | |
|---|---|---|---|
| HIV-1 isolate | Without Nevirapine | With 50 µM Nevirapine | Inhibition of RT. (%) |
| X267-1 | $7.1 \times 10^{-7}$ | $9.1 \times 10^{-9}$ | 98.7 |
| | $7.2 \times 10^{-8}$ | N.D. | 100 |
| | $6.9 \times 10^{-9}$ | N.D. | 100 |
| X403-4 | $4.4 \times 10^{-7}$ | $3.7 \times 10^{-7}$ | 16 |
| | $8.2 \times 10^{-9}$ | $8.4 \times 10^{-9}$ | 0 |
| | $4.1 \times 10^{-7}$ | $5.0 \times 10^{-7}$ | 0 |
| W786-6 | $5.6 \times 10^{-8}$ | $7.7 \times 10^{-8}$ | 0 |

N.D. = not detected
*Mean RT activity observed in at least three different experiments performed in duplicate The specificity of the AMP-RT assay was analyzed to determine whether Amp-RT testing in the presence of 50 µM nevirapine only detected resistance in RTs carrying mutations associated with resistance to nevirapine, and not in RTs carrying other unrelated resistance mutations. Table 5, below, shows that RTs carrying the Y181C and K103N mutations (N119 and L6KL5, respectively) were highly resistant to nevirapine (inhibition values of 0% and 7%). In contrast, viruses containing mutations associated with AZT or 3TC resistance were all found to be susceptible to nevirapine. RT activity from a virus carrying the V106A mutation (HIV-$1_{RTMDR1}$/MT-2) was partially inhibited with 50 µM nevirapine, demonstrating a lower level of resistance to nevirapine compared to RT with the Y181C mutation. Based on these results, Amp-RT conditions containing 50 µM nevirapine were used as a primary screening assay for nevirapine resistance in all subsequent testing of plasma samples unless otherwise indicated.

TABLE 5

Inhibition by 50 µM Nevirapine of Amp-RT Activity from AZT-, 3TC-, ddI-, and Nevirapine-Resistant HIV-1 Reference Viruses

| Reference virus | Mutations | Phenotype | Inhibition of RT by Nevirapine |
|---|---|---|---|
| HIV-$1_{RTMC}$/MT-2 | 67N/70R/215F/219Q | AZT-resistant | 91.8% |
| M184V$_{pitt}$ | 184V | 3TC-resistant | 98.8% |
| HIV-$1_{RTMDR1}$/MT-2 | 74V/41L/106A/215Y | AZT-, ddI-, nevirapine-resistant | 43% |
| L6KL5 | 103N/75I/77L/116Y/151M | 3TC-, ddI-, ddC-, nevirapine-resistant | 0 |
| M184V/Y181C$_{EU}$ | 184V/181C | 3TC/nevirapine-resistant | 0 |
| N119 | 181C | nevirapine-resistant | 7% |

Figure 7:
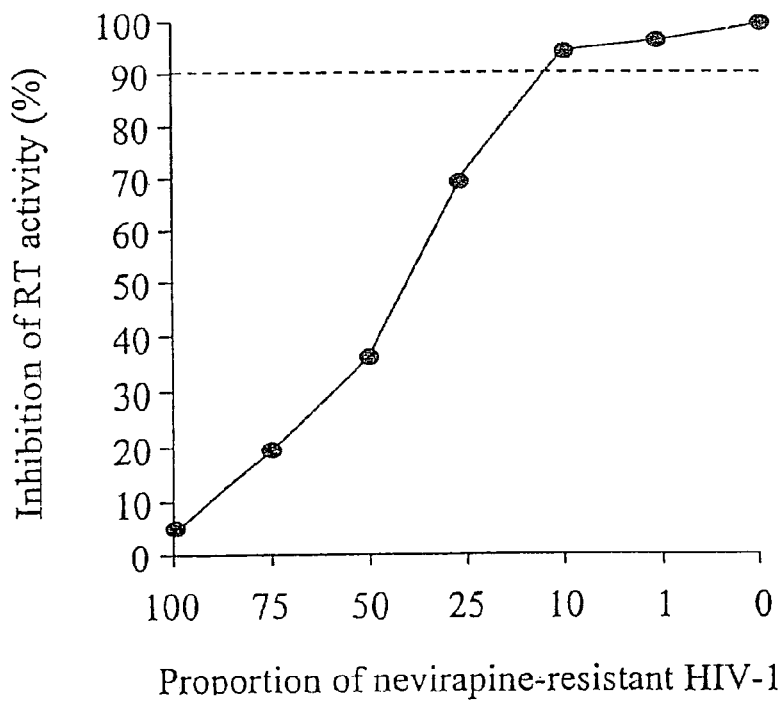
FIG. 7 is a graph of proportion of nevirapine-resistant HIV-1 versus inhibition of reverse transcriptase activity showing an analysis of mixtures of wild type and nevirapine-resistant HIV-1 by the Amp-RT assay described herein.

Detection Threshold of Resistant Virus in Mixtures of Wild Type and Nevirapine-resistant Viruses To determine the detection threshold of the assay, a sensitive (X,267-1) HIV-1 clinical isolate and a nevirapine-resistant (W786-6) HIV-1 clinical isolate were mixed at different proportions and tested for evidence of resistance. Both isolates were adjusted to similar levels of RT activity before virus mixtures were prepared. As shown in FIG. 7, values of RT inhibition of >99% were only observed when the sensitive isolate was tested. In contrast, mixtures containing 10% of resistant viruses and 90% of sensitive viruses had RT inhibition values of 94%, suggesting that only sensitive RTs were inhibited by nevirapine and indicating an assay detection threshold for resistant viruses of ~10%. The observed level of RT inhibition in the virus mixtures decreased as the ratio of resistant-to-sensitive viruses increased. For instance, mixtures containing 25% or 75% of resistant viruses had levels of RT inhibition of 80% and 29%, respectively.

Analysis of Phenotypic Resistance to Nevirapine in Plasma and Correlation with Mutations at Codon 181

To validate the assay for detection of phenotypic resistance to nevirapine in HIV-1 from plasma, 30 plasma specimens collected from four patients before and during nevirapine monotherapy (patients N12N06, N07, and E01) were tested. Phenotypic resistance determined by Amp-RT was compared with the relative proportion of mutations at codon 181 in HIV-1 from plasma (MUT/GNR ratio).

Figure 8:
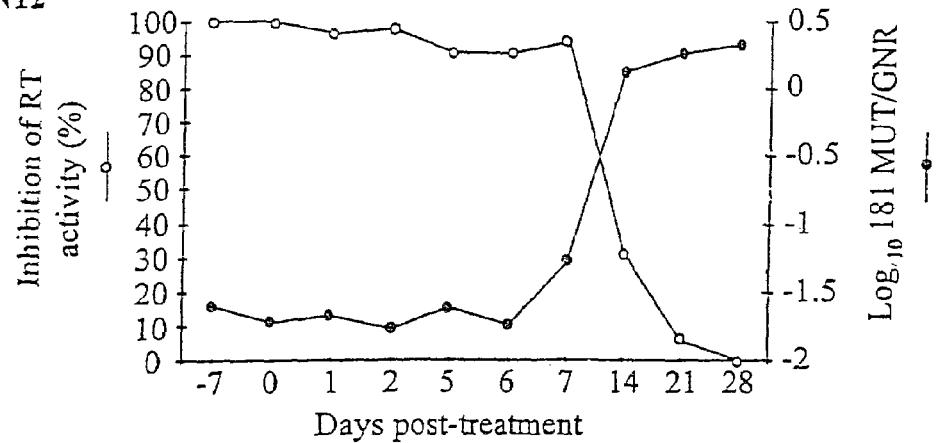
FIG. 8 is a series of three graphs showing days post-treatment with nevirapine versus inhibition of reverse transcriptase activity for three HIV-1-infected patients.
Figure 8:
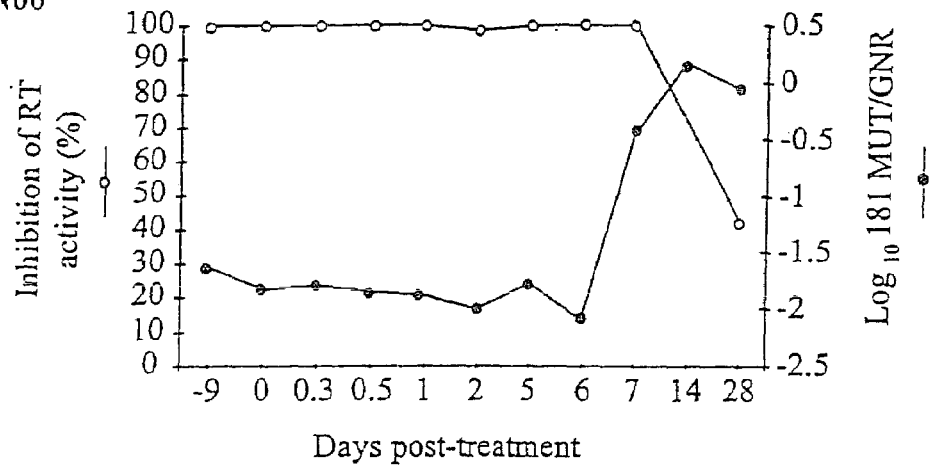
Figure 8:
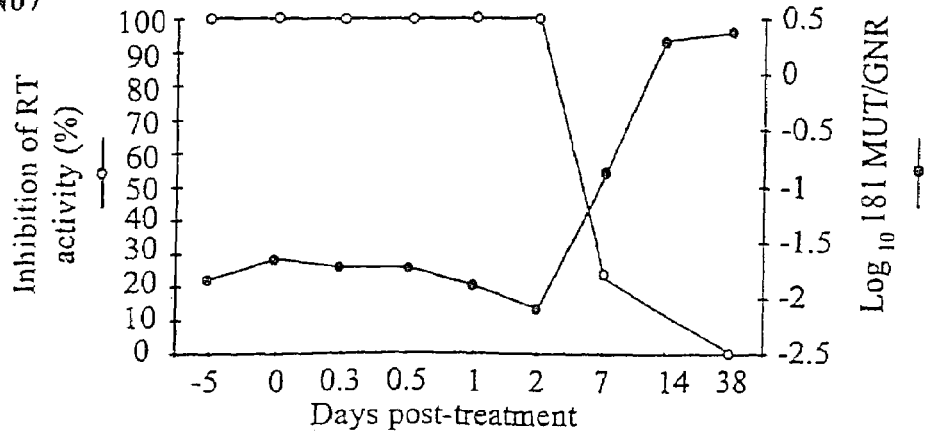

FIG. 8 illustrates the kinetics of detection of both Y181C mutation and evidence of phenotypic resistance to nevirapine in the Amp-RT assay as indicated by decreased level of inhibition of RT in three patients. Patient E01 had only 2 plasma samples taken before and after 28 days of treatment and is not included in the figure. The results show a clear correlation between the decrease in the levels of RT inhibition and the emergence of viruses carrying the Y181C mutation. All samples collected before therapy (n=7) or during the first six days of treatment (n=14) were found to be sensitive to nevirapine, with mean RT inhibition values of 99.3% (range=100%-99.5%) and 98.2% (range=100%-90.4%), respectively. The MUT/GNR ratio in these samples ranged from 0.01 to 0.03 (mean=0.02) before therapy and from 0.008 to 0.02 (mean=0.02) during the first six days of treatmaent, indicating the absence of detectable Y181 C mutation in these samples. The first evidence of phenotypic resistance to nevirapine was found in two samples collected at days 7 and 14 of treatment (patients N07 and N12; RT inlhibitionl values of 24% and 32%, respectively). The observed phenotypic resistance to nevirapine correlated with the detection of the Y181C mutation (MUT/GNR ratio of 0.12 and 1.34respectively). From two other samples collected after 7 days of treatment, one (patient N12) had borderline susceptibility to nevirapine (RT inhibition of 94%) and a level of Y181C mutation (MUT/GNR ratio of 0.05) at the detection threshold of the genotypic assay (defined as a MUT/GNR ratio of 0.03). The other sample (patient N06) had evidence of detectable Y181C mutation (MUT/GNR ratio of 0.4) and WT susceptibility to nevirapine (RT inhibition value of 100%). The discordant results observed in this particular sample from patient N06 is unexpected because other samples with MUT/GNR ratios of 0.4 and 0.12 had detectable phenotypic resistance by the Amp-RT assay. Phenotypic testing by other methods may be necessary to clarify nevirapine susceptibility in this particular sample.

All samples obtained after more than two weeks of treatment bad high levels of phenotypic resistance to nevirapine, with a mean RT inhibition value of 13.82% (range=0%-43.1%) and mean MUT/GINR ratio of 1.45 (range=0.4-2.16). These results indicate a clear correlation between detection of phenotypic resistance to nevirapine by the Amp-RT assay and emergence of the Y181C mutation and suggest that the assay may be used as a rapid tool for clinical monitoring of phenotypic resistance to nevirapine in HIV-1 from plasma.

Amp-RT $IC_{50}$ Values for Nevirapine in Plasma HIV-1

To quantitate the level of nevirapine resistance, the Amp-RT $IC_{50}$ values in longitudinal samples from patient N12 by testing the plasma RT in the presence of several concentrations of nevirapine were determined. The Amp-RT $IC_{50}$ values observed at days 6 and 7 of therapy (approximately 15 µM) were similar to those observed in WT isolates, indicating WT susceptibility to nevirapine. In contrast, no inhibition was observed in two samples collected at days 21 and 28 of treatment at all concentrations of nevirapine used, resulting in an Amp-RT $IC_{50}$>100 uM. The observed increase in Amp-RT $IC_{50}$ values correlated with the genotypic detection of the Y181C mutation (MUT/GNR ratio of 0.018 and 0.05 at 6 and 7 days, respectively, compared to 1.81 and 2.16 at 21 and 28 days, respectively). These results further validated the use of 50 µM nevirapine in Amp-RT reactions for rapid screening of phenotypic resistance to this drug.

Figure 9:
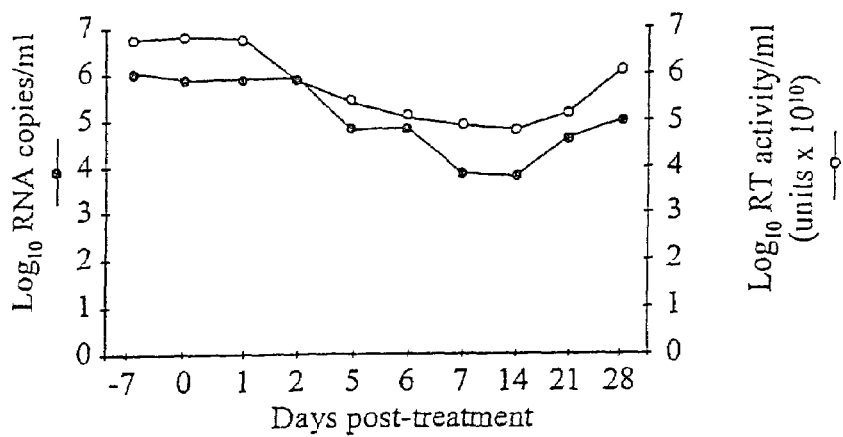
FIG. 9 is a series of three graphs showing days post-treatment with nevirapine versus $\log_{10}$ RNA copies/ml for three HIV-1-infected patients.
Figure 9:
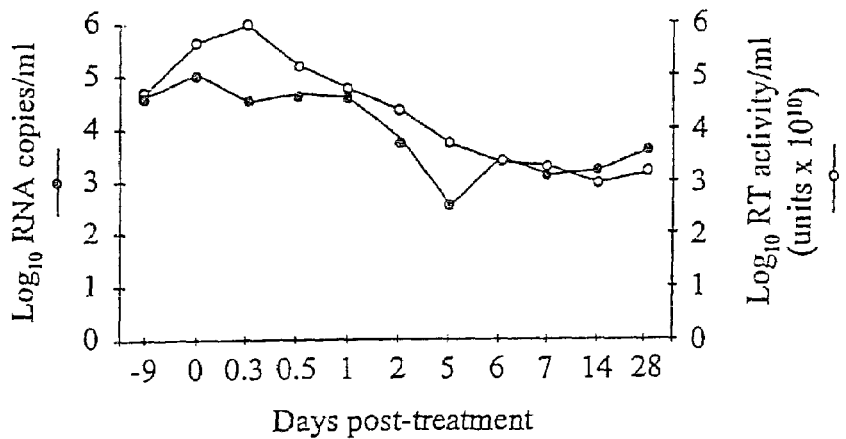
Figure 9:
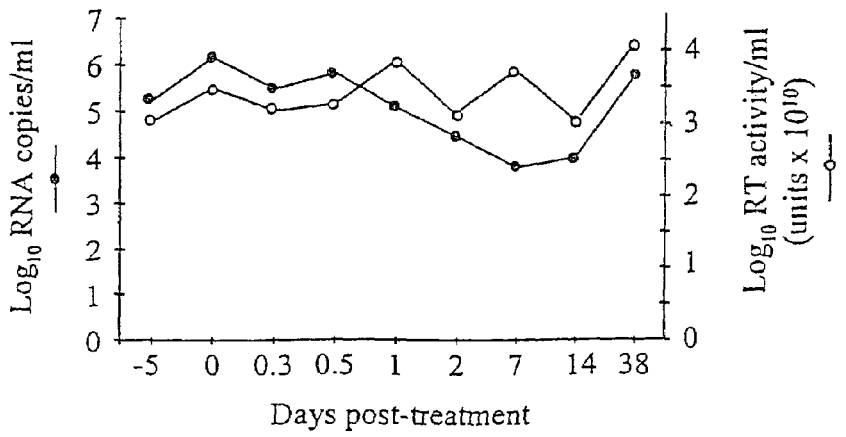

Quantitation of Plasma RT Activity by the Amp-RT Assay and Correlation with HIV-1 RNA Levels The kinetics of RT-based viral loads were analyzed and compared with the RNA viral load determined by RT-PCR. FIG. 9 shows levels of both RNA and RT in plasma samples from the three patients who had more than two viral load determinations (patients N12, N06, and N07). RT-based viral loads were derived from Amp-RT reactions made with no nevirapine. The results demonstrated that plasma viral loads measured by RT or RNA were similar for each of the three patients, indicating that the Amp-RT assay may also be used to monitor changes in viral load following antiretroviral therapy.

Conclusion

The Amp-RT assay has several advantages compared to conventional culture-based assays. First, because results are obtained in 1-2 days, the assay provides rapid information on resistance that may assist clinicians in treatment decisions. Second, the assay measures directly phenotypic resistance in HIV-1 from plasma samples, and therefore, does not have selection bias associated with virus isolation in culture.

Phenotypic testing conventionally measures nevirapine susceptibility by analysis of inhibition by several drug concentrations and by determining $IC_{50}$ values. The Amp-RT testing strategy relies on the use of a single drug concentration (50 µM) for rapid screening of nevirapine resistance in plasma. Several observations validate this testing approach. First, complete inhibition of wild type HIV-1 RTs was achieved in Amp-RT reactions containing 50 µM nevirapine. Second, lack of inhibition was only observed in RTs carrying nevirapine-resistance mutations, including Y181C, V106A, K103N, Y190A, G190A, and Y188L. Third, results were reproducible within a wide range of RT levels. Fourth, RT susceptibility results correlated with levels of genotypic markers of resistance (Y181C mutation) in plasma samples. All these findings indicate that analysis of RT inhibition using 50 µM nevirapine in the Amp-RT assay can be used to rapidly screen for nevirapine resistance. However, this testing approach does not provide $IC_{50}$ values for nevirapine. Additional Amp-RT testing with several concentrations of nevirapine is required for quantitating the level of resistance, as shown in four samples from patient N12.

In addition to phenotypic resistance to nevirapine, the assay provides information on levels of functional RT in plasma. The observed correlation between levels of functional RT activity in plasma and HIV-1 RNA viral loads indicates that the Amp-RT testing is suitable for monitoring viral loads following antiretroviral treatment.

The non nucleoside HIV-1 RT inhibitors comprise a series of structurally diverse compounds that share a common mechanism of action and bind to a common site of the enzyme. Some of the mutations associated with nevirapine resistance confer cross-resistance among this class of compounds. For instance, recombinant viruses carrying the Y181C mutation are highly resistant to delavirdine and loviride in addition to nevirapine and the K103N mutation confers cross-resistance to efavirenz, delavirdine, and loviride. The foregoing results, indicating that the assay detects resistance mediated by these mutations, suggest that this approach could be adapted for detection of resistance to other nonucleoside. RT inhibitors, such as efavirenz, proposed for treatment of HIV-1-infected individuals.

EXAMPLE 3

Rapid Phenotypic Assay for Detecting Multiple Nucleoside Analog Reverse Transcriptase Inhibitor-resistant Human Immunodeficiency Virus Type 1 in Plasma Zidovudine (AZT) and other nucleoside analog reverse transcriptase inhibitors (NRTIs) like zalcitabine and didanosine used for treatment of persons infected with human immunodeficiency virus type 1 (HIV-1) can select for viruses with Q151M and other associated mutations (i.e., A62V, S68G, V751F77L, F116Y) in the reverse transcriptase (RT) enzyme. These mutations confer resistance to multiple nucleoside analogs, thereby compromising the efficacy of this class of drugs. Therefore, recognition of this is important in the effective prevention, treatment and/or amelioration of HIV infection. Specifically, failure to recognize the presence of the resistant species in the infected host (i.e., patient) allows prolonged use of drugs and therapies that are no longer the optimally effective therapy or treatment. Thus, an ability to recognize and identify (detect) MNR HIV-1 in a patient is critical for optimal care and treatment.

Presently available methods and techniques for detecting the presence of MNR HIV strains or for ascertaining the relative character of a population of viruses in an infected host are not necessarily optimal. Presently available phenotypic assays for detection of multiple nucleoside analog resistant (MNR) HIV-1 require testing for each NRTI individually. This is generally too complicated, costly and burdensome for cost-effective use. Herein, an enzymatic RT assay that uses resistance to AZT triphosphate (AZT-TP) as a diagnostic biochemical marker of MNR HIV-1 is described. This assay exploits the different biochemical mechanisms for AZT-resistance conferred by either Q151M or T215Y/F mutations and the inability of conventional RT assays to detect T215Y/F-associated AZT resistance. The assay detects RT activity directly in plasma by using Amp-RT, an ultra-sensitive PCR-based RT assay. Thus, it can be shown that enzymatic resistance to AZT-TP is specific to MNR RT and is distinguishable from both wild type (WT) and RT containing classical AZT-resistant mutations (D67N, K70R, T215Y/F, K219Q). Compared to WT, MNR HIV-1 RT had 5- to 36-fold increases in the concentration of drug required to inhibit 50% ($IC_{50}$) of RT activity, depending on the presence of Q151M alone or with additional MNR mutations. A screening assay utilizing 1 µM AZT-TP was developed and was validated on 14 reference isolates, 37 plasma specimens, and 7 patient-derived viruses. Twenty three specimens were found to have reduced susceptibility to AZT-TP, and all had Q151M. In contrast, 21 specimens were sensitive to AZT-TP, of which 12 had WT genotypes, 4 had T215Y/F, and 5 had T69S-insertions along with T215Y/F mutations. This RT-based phenotypic assay provides a specific and rapid tool for the direct identification and monitoring of Q151M-associated MNR HIV-1 in plasma.

Introduction

The nucleoside reverse transcriptase inhibitors (NRTIs) zidovudine (AZT), lamivudine, zalcitabine, didanosine, stavudine, and abacavir are important components of current anti-human immunodeficiency virus type-1 (HIV-1) treatment regimens (Carpenter et al., "Antiretroviral therapy in adults: updated recommendations of the International AIDS Society-USA Panel. Antiretroviral therapy in adults: updated recommendations of the International AIDS Society-USA Panel," *JAMA* 283:381-390 (2000)). However, HIV-1 strains resistant to several NRTIs emerge in many patients treated with NRTIs, thus limiting the clinical benefit of this class of drugs. The resistance to several NRTIs is conferred by three different patterns of mutations in HIV-1 RT. One pattern is normally associated with acquisition of the Q151M mutation in the polymerase domain of RT. This mutation confers multiple-NRTI-resistance to all currently approved NRTIs (Shirasaka et al., "Changes in drug sensitivity of human immunodeficiency virus type I during therapy with azidothymidine, dideoxycytidine, and dideoxyinosine: an in vitro comparative study," *Proc. Nat. Acad. Sci. USA* 90: 562-566 (1993); Ueno et al., "Enzymatic characterization of human immunodeficiency virus type 1 reverse transcriptase resistant to multiple 2',3'-dideoxynucleoside 5'-triphosphates," *J. Biol.*

Chem. 270: 23605-23611 (1995); Kavlick et al., "Emergence of multi-dideoxynucleoside-resistant human immunodeficiency virus type 1 variants, viral sequence variation, and disease progression in patients receiving antiretroviral chemotherapy," *J. Infect. Dis.* 177: 1506-1513 (1998); Schist et al., "Multiple dideoxynucleoside analogue-resistant (MddNR) HIV-1 strains isolated from patients from different European countries," *AIDS* 12: 2007-2015 (1998); Van Laethem et al., "Patient HIV-1 strains carrying the multiple nucleoside resistance mutations are cross-resistant to abacavir," *AIDS* 14: 469-471 (2000)). However, these viruses remain sensitive to the nucleotide RTI tenofovir (Miller et al., "Antiviral activity of tenofovir (PMPA) against nucleoside-resistant clinical HIV samples," *Nucleosides Nucleotides Nucleic Acids* 20: 1025-1028 (2001)). The level of resistance to NRTIs increases with the acquisition of additional multiple-NRTI-resistant (MNR) mutations (A62V, S68G, V75J, F77L, and F116Y). MNR HIV-1 strains have been observed in about 3% of the HIV-1 patients treated with AZT and zalcitabine-didanosine and occasionally in patients receiving other AZT-containing regimens (Shirasaka et al., "Changes in drug sensitivity of human immunodeficiency virus type 1 during therapy with azidothymidine, dideoxycytidine, and dideoxyinosine: an in vitro comparative study," *Proc. Nat. Acad. Sci. USA* 90: 562-566 (1993); Schmit et al., "Multiple dideoxynucleoside analogue-resistant (MddNR) HIV-1 strains isolated from patients from different European countries," *AIDS* 12: 2007-2015 (1998); Shafer et al., "Drug resistance and heterogeneous long-term virologic responses of human immunodeficiency virus type 1-infected subjects to zidovudine and didanosine combination therapy. The AIDS Clinical Trials Group 143 Virology Team," *J. Infect. Dis.* 172: 70-78 (1995); Schmit et al., "Multiple drug resistance to nucleoside analogues and nonnucleoside reverse transcriptase inhibitors in an efficiently replicating human immunodeficiency virus type 1 patient strain," *J. Infect. Dis.* 174: 962-968 (1996); Maeda et al., "Altered drug sensitivity, fitness, and evolution of human immunodeficiency virus type 1 with pol gene mutations conferring multi-dideoxynucleoside resistance," *J. Infect. Dis.* 177: 1207-1213 (1998); Van Vaerenbergh et al., "Prevalence and characteristics of multinucleoside-resistant human immunodeficiency virus type 1 among European patients receiving combinations of nucleoside analogues," *Antimicrobial Agents and Chemotherapy* 44: 2109-2117 (2000)).

Another pattern of resistance to NRTIs is associated with the selection of classical AZT resistance-related mutations, T215Y/F, M41L, D67N, K70R, and K219Q/E. Viruses with these genotypes confer a high level (>100-fold) of resistance to AZT (Van Vaerenbergh et al., "Prevalence and characteristics of multinucleoside-resistant human immunodeficiency virus type 1 among European patients receiving combinations of nucleoside analogues," *Antimicrobial Agents and Chemotherapy* 44: 2109-2117 (2000)). The T215Y mutation, which plays a pivotal role in conferring resistance to AZT, can also be selected less frequently by stavudine (Mouroux et al., "Conditions of "thymidine analog mutations" (TAMs) in naive patients treated with different combinations of d4T," *Pathology Biology* 48: 508-512 (2000)). A third pathway for NRTI resistance is associated with insertions of two amino acids such as SS, SG, AG, SA, EA, or TS following the T69S/A codon in RT. These insertions generally occur in viruses that contain classical AZT resistance-related mutations and confer low level resistance to many NRTIs (Van Vaerenbergh et al., "Prevalence and characteristics of multinucleoside-resistant human immunodeficiency virus type 1 among European patients receiving combinations of nucleoside analogues," *Antimicrobial Agents and Chemotherapy* 44: 2109-2117 (2000); Winters et al., "A 6-base pair insert in the reverse transcriptase gene of human immunodeficiency virus type 1 confers resistance to multiple nucleoside inhibitors," *J. Clin. Invest.* 102: 1769-1775 (1998); Larder et al., "A family of insertion mutations between codons 67 and 70 of human immunodeficiency virus type 1 reverse transcriptase confer multinucleoside analog resistance," *Antimicrobial Agents and Chemotherapy* 43: 1961-1967 (1999); de Jong et al., "Insertion of two amino acids combined with changes in reverse transcriptase containing tyrosine-215 of HIV-1 resistant to multiple nucleoside analogs," *AIDS* 13: 75-80 (1999); Mas et al., "Role of a dipeptide insertion between codons 69 and 70 of HIV-1 reverse transcriptase in the mechanism of AZT resistance," *EMBO J.* 19: 5752-5761 (2000)).

Two distinct biochemical mechanisms have been proposed for AZT resistance in mutant HIV-1 RT. The first includes loss of affinity for AZT triphosphate (AZT-TP) and is associated with the Q151M mutation (Ueno et al., "Enzymatic characterization of human immunodeficiency virus type 1 reverse transcriptase resistant to multiple 2',3'-dideoxynucleoside 5'-triphosphates," *J. Biol. Chem.* 270: 23605-23611 (1995); Ueno et al., "Comparative enzymatic study of HIV-1 reverse transcriptase resistant to 2',3'-dideoxynucleoside analogs using the single-nucleotide incorporation assay," *Biochemistry* 36: 1092-1099 (1997); Sluis-Cremer et al., "Molecular mechanisms of HIV-1 resistance to nucleoside reverse transcriptase inhibitors (NRTIs)," *Cell. Mol. Life Sci.* 57: 1408-1422 (2000)). The second mechanism is attributed to the T215Y/F mutation complex and involves enhanced removal of incorporated AZT-monophosphate (AZT-MP) from terminated DNA (Mas et al., "Role of a dipeptide insertion between codons 69 and 70 of HIV-1 reverse transcriptase in the mechanism of AZT resistance, "*EMBO J.* 19: 5752-5761 (2000); Arion et al., "Phenotypic mechanism of HIV-1 resistance to 3'-azido-3'-deoxythymidine (AZT): increased polymerization processivity and enhanced sensitivity to pyrophosphate of the mutant viral reverse transcriptase," *Biochemistry* 37: 15908-15917 (1998); Meyer et al., "A mechanism of AZT resistance: an increase in nucleotide-dependent primer unblocking by mutant HIV-1 reverse transcriptase," *Mol. Cell* 4:35-43 (1999); Lennerstrand et al., "Correlation between viral resistance to zidovudine (AZT) and resistance at the reverse transcriptase level found for a panel of HIV-1 mutants," *J. Virology* 75: 7202-7205 (2001)). Excision of AZT-MP requires the presence of adenosine-triphosphate (ATP) or pyrophosphate (PPi) that are thought to serve as acceptors for the excised AZT-MP residue. Both mechanisms of AZT resistance can be discriminated in enzymatic RT assays. The Q151M mutant RT shows increased Ki (enzyme-inhibition dissociation constant) values for AZT-TP in standard RT assays compared to WT RT (Ueno et al., "Comparative enzymatic study of HIV-1 reverse transcriptase resistant to 2',3'-dideoxynucleotide analogs using the single-nucleotide incorporation assay," *Biochemistry* 36: 1092-1099 (1997); Lennerstrand et al., "Correlation between viral resistance to zidovudine (AZT) and resistance at the reverse transcriptase level found for a panel of HIV-1 mutants," *J. Virology* 75: 7202-7205 (2001)). In contrast, WT and the T215Y/F mutant have similar Ki values for AZT-TP and are thus indistinguishable from each other using these RT assays (Ueno et al., "Enzymatic characterization of human immunodeficiency virus type 1 reverse transcriptase resistant to multiple 2',3'-dideoxynucleoside 5'-triphosphates," *J. Biol. Chem.* 270: 23605-23611 (1995); Ueno et al., "Comparative enzymatic study of HIV-1 reverse transcriptase resistant to 2',3'-dideoxynucleotide analogs using the single-nucleotide incorporation assay," *Biochemistry* 36: 1092-1099 (1997); Lennerstrand et al., "Correlation between viral resistance to zidovudine (AZT) and resistance at the reverse transcriptase level found for a panel of HIV-1 mutants," *J. Virology* 75: 7202-7205 (2001); Lacey et al., "Biochemical studies on the reverse transcriptase and RNase H activities from human immunodeficiency virus strains resistant to 3'-azido-3'-deoxythymidine," *J. Biol. Chem.* 267: 15789-15794 (1992); Carroll et al., "Sensitivity of HIV-1 reverse transcriptase and its mutants to inhibition by azidothymidine triphosphate," *Biochemistry* 33: 2113-2120 (1994); Kerr et al., "Pre-steady-state kinetic characterization of wild type and 3'-azido-3'-deoxythymidine (AZT) resistant human immunodeficiency virus type 1 reverse transcriptase: implication of RNA directed DNA polymerization in the mechanism of AZT resistance," Biochemistry 36:14064-14070 (1997); Krebs et al., "Single-step kinetics of HIV-1 reverse transcriptase mutants responsible for virus resistance to nucleoside inhibitors zidovudine and 3-TC," *Biochemistry* 36:10292-10300 (1997)). However, resistance to AZT-TP can be observed with mutant RT carrying T215Y/F using special enzymatic assays which have been modified by the addition of ATP or PPi or tailored to measure rates of AZT unblocking (Mas et al., "Role of a dipeptide insertion between codons 69 and 70 of HIV-1 reverse transcriptase in the mechanism of AZT resistance," *EMBO J.* 19: 5752-5761 (2000); Arion et al., "Phenotypic mechanism of HIV-1 resistance to 3'-azido-3'-deoxythymidine (AZT): increased polymerization processivity and enhanced sensitivity to pyrophosphate of the mutant viral reverse transcriptase," *Biochemistry* 37: 15908-15917 (1998); Meyer et al., "A mechanism of AZT resistance: an increase in nucleotide-dependent primer unblocking by mutant HIV-1 reverse transcriptase," *Mol. Cell* 4:35-43 (1999); Lennerstrand et al., "Correlation between viral resistance to zidovudine (AZT) and resistance at the reverse transcriptase level found for a panel of HIV-1 mutants," *J. Virology* 75: 7202-7205 (2001)). AZT-resistant HIV-1 RT carrying T69S insertions only has also been shown to have ATP-dependent enhanced removal of AZT-MP (Mas et al., "Role of a dipeptide insertion between codons 69 and 70 of HIV-1 reverse transcriptase in the mechanism of AZT resistance," *EMBO J.* 19: 5752-5761 (2000); Arion et al., "Phenotypic mechanism of HIV-1 resistance to 3'-azido-3'-deoxythymidine (AZT): increased polymerization processivity and enhanced sensitivity to pyrophosphate of the mutant viral reverse transcriptase," *Biochemistry* 37: 15908-15917 (1998)).

The knowledge of the biochemical basis of AZT resistance associated with different mutations is also important for the development of specific drug resistance tests that are based on RT assays. At present, drug resistance testing is recommended to guide the choice of new drug regimens after initial or multiple treatment failures (Hirsch et al., "Antiretroviral Drug Resistance Testing in Adult HIV-1 Infection: Recommendations of an International AIDS Society—USA Panel," *JAMA*, 283: 2417-2426 (2000); The EuroGuidelines Group for HIV Resistance, "Clinical and laboratory guidelines for the use of HIV-1 drug resistance testing as part of treatment management: recommendations for the European setting. The EuroGuidelines Group for HIV resistance." *AIDS* 2001; 16:309-320 (2001)). Drug resistance testing is currently done by genotypic or culture-based phenotypic methods (Hirsch et al., "Antiretroviral drug resistance testing in adults with HIV infection: implications for clinical management," International AIDS Society—USA Panel. Journal of the American Medical Association 279:1984-1991 (1998)). The most common genotypic methods detect resistance-related mutations by nucleotide sequencing, while recombinant virus assays are the phenotypic assays predominantly used to measure drug susceptibility of patient-derived viruses. Since both testing approaches are complex, labor intensive, and expensive, simpler and less expensive drug resistance assays are critically needed. A new approach for phenotypic drug resistance testing, also described in Examples 1 and 2 not based on virus cultures, but instead on the use of rapid and simple biochemical assays that directly measure the susceptibility of RT activity in plasma to RT inhibitors has been described (Garcia Lerma et al., "A rapid non-culture-based assay for clinical monitoring of phenotypic resistance of human immunodeficiency virus type 1 to lamivudine (3TC)," *Antimicrobial Agents and Chemotherapy* 43: 264-270 (1999); Vazquez-Rosales et al., "Rapid screening of phenotypic resistance to nevirapine by direct analysis of HIV type 1 reverse transcriptase activity in plasma," *AIDS Research and Human Retroviruses* 15: 1191-1200 (1999)). This testing approach was made possible by the use of Amp-RT, a PCR-based ultrasensitive RT assay that is capable of detecting very low level RT activity in plasma (Heneine et al., "Detection of reverse transcriptase by a highly sensitive assay in sera from persons infected with human immunodeficiency virus type 1," *J. Infect. Dis.* 171: 1210-1216 (1995); Yamamoto et al., "Highly sensitive qualitative and quantitative detection of reverse transcriptase activity: optimization, validation, and comparative analysis with other detection systems," *J. Virol. Methods* 61: 135-143 (1996); Garcia Lerma et al., "Measurement of human immunodeficiency virus type 1 plasma virus load based on reverse transcriptase (RT) activity: evidence of variabilities in levels of virion-associated RT," *J. Infect. Dis.* 177: 122.1-1229 (1998)). As described herein in Examples 1 and 2 and in cited literature, it has been shown that such testing can successfully detect lamivudine- or nevirapine-resistant HIV-1 in plasma (Garcia Lerma et al., "A rapid non-culture-based assay for clinical monitoring of phenotypic resistance of human immunodeficiency virus type 1 to lamivudine (3TC)," *Antimicrobial Agents and Chemotherapy* 43: 264-270 (1999); Vazquez-Rosales et al., "Rapid screening of phenotypic resistance to nevirapine by direct analysis of HIV type 1 reverse transcriptase activity in plasma," *AIDS Research aid Human Retroviruses* 15: 1191-1200 (1999); Garcia-Lerma et al., "Quantitation of human immunodeficiency virus type 1 group O load in plasma by measuring reverse transcriptase activity," *J. Clin. Micro.* 2000; 38: 402-405 (2000)).

This example describes a unique and novel development using another Amp-RT-based assay for the specific identification of viruses with the MNR phenotype conferred by the Q151M mutation. The assay uses enzymatic resistance of plasma HIV-1 RT activity to AZT-TP as a diagnostic marker of the Q151M-mediated MNR phenotype. Correspondingly, this assay can distinguish MNR viruses from either WT or AZT-resistant viruses containing T215Y/F mutations.

Materials and Methods

Four plasma samples and HIV-1SUM8HIV-1SUM9HIV-1SUM10HIV-1SUM12and HIV-1SUM13 were obtained from Hiroaki Mitsuya (National Cancer Institute, NIH, Bethesda). HIV-1xxBRUpitt, HIV-1M184Vpitt and HIV-1M184V/Y181CEU were obtained from Raymond F. Schinazi (Emory University/Veterans Affairs Medical Center, Atlanta). HIV-1HXB2xxHIV-1LAI, HIV-1RTMF/MT-2HIV-1RTMDR1/MT-2and HIV-1RTMC/MT-2 were obtained from the AIDS Research and Reference Reagent Program, Division of AIDS, NIAID, NIH (Rockville, Md.).

Susceptibility of RT Activity to AZT-TP and other NRTI-TPs

The RT test used in this study was the Amp-RT assay which uses a known non-retroviral heteropolymeric RNA template derived from the encephalomyocarditis virus (EMCV) genome and an EMCV-specific primer (Heneine et al., "Detection of reverse transcriptase by a highly sensitive assay in sera from persons infected with human immunodeficiency virus type 1, " *J. Infect. Dis.* 171: 1210-1216 (1995); Yamamoto et al., "Highly sensitive qualitative and quantitative detection of reverse transcriptase activity: optimization, validation, and comparative analysis with other detection systems," *J. Virol. Methods* 61: 135-143 (1996); Garcia Lerma et al., "Measurement of human immunodeficiency virus type 1 plasma virus load based on reverse transcriptase (RT) activity: evidence of variabilities in levels of virion-associated RT," *J. Infect. Dis.* 177: 1221-1229 (1998)). The RT-generated EMCV cDNA is detected by PCR amplification and subsequently quantitated by probing of the amplified product with an internal EMCV-specific oligonucleotide in a streptavidine-digoxigenin ELISA-based hybridization as previously described (Garcia Lerma et al., "Measurement of human immunodeficiency virus type 1 plasma virus load based on reverse transcriptase (RT) activity: evidence of variabilities in levels of virion-associated RT," *J. Infect. Dis.* 177: 1221-1229 (1998)).

The susceptibility of HIV-1 RT activity from viral isolates or plasma samples to AZT-TP was determined based on the level of inhibition in RT activity produced by the drug. The level of inhibition was measured by performing quantitative Amp-RT reactions in the absence and presence of several AZT-TP concentrations (0.1-50 µM). AZT-TP concentrations inhibiting 50% and 90% ($IC_{50}$ and $IC_{90}$) of RT activity were determined as previously described (Garcia Lemma et al., "A rapid non-culture-based assay for clinical monitoring of phenotypic resistance of human immunodeficiency virus type 1 to lamivudine (3TC)," *Antimicrobial/Agents and Chemotherapy* 43: 264-270 (1999); Vazquez-Rosales et al., "Rapid screening of phenotypic resistance to nevirapine by direct analysis of HIV type 1 reverse transcriptase activity in plasma," *AIDS Research and Human Retroviruses* 15: 1191-1200 (1999)). For culture supernatant, 10 µl samples were used directly in the Amp-RT assay. Plasma specimens were first clarified by centrifugation at 10,000 g for 5 min and then ultracentrifuged in a fixed angle rotor at 99,000×g for 1 hour at 4° C. The viral pellet was suspended in RT buffer (50 mM Tris-HCl, 50 mM KCl, 10 mM $MgCl_2$) in a volume equal to that of the plasma used for pelleting. Ten microliter aliquots of resuspended virus pellets were mixed with the RT buffer containing 10 ng of EMCV RNA template, 10 units of RNasin, 0.6% NP-40, 100 ng of the 5'-biotin-labeled EMCR2 antisense primer, 1 mM EGTA, 2 mM dithiothreitol, 50 mM Tris-HCl, 50 mM KCl, 10 mM MgCl2, 15 µM of dTTP, and 20 µM of each dCTP, dGTP, and dATP. The RT reaction was carried out at 37° C. for 2 hours and was followed by PCR amplification (Heneine et al., "Detection of reverse transcriptase by a highly sensitive assay in sera from persons infected with human immunodeficiency virus type 1," *J. Infect. Dis.* 171: 1210-1216 (1995); Yamamoto et al., "Highly sensitive qualitative and quantitative detection of reverse transcriptase activity: optimization, validation, and comparative analysis with other detection systems," *J. Virol. Methods* 61: 135-143 (1996); Garcia Lerma et al., "Measurement of human immunodeficiency virus type 1 plasma virus load based on reverse transcriptase (RT) activity: evidence of variabilities in levels of virion-associated RT," *J. Infect. Dis.* 177: 1221-1229 (1998)). For quantitation of RT levels, a standard curve was generated by using known RT units from a reference HIV-1 stock (kindly provided by the Virology Quality Assurance Laboratory, Rush-Presbyterian-St. Luke's Medical Center, Chicago, Ill.). This virus stock, referred to as VQA, has been shown to contain 0.96×10-10 units of RT activity per virion (Garcia Lerma et al., "Measurement of human immunodeficiency virus type 1 plasma virus load based on reverse transcriptase (RT) activity: evidence of variabilities in levels of virion-associated RT," *J. Infect. Dis.* 177: 1221-1229 (1998)). Quantitative detection of Amp-RT products was made by using an ELISA-based, nonradioactive, oligoprobing system with an internal EMCV-specific probe, as previously described (Garcia Lerma et al., "Measurement of human immunodeficiency virus type 1 plasma virus load based on reverse transcriptase (RT) activity: evidence of variabilities in levels of virion-associated RT," *J. Infect. Dis.* 177: 1221-1229 (1998)). All samples were tested in duplicate or triplicate and within the linear range of RT activity determined for this assay ($\sim 1.82 \times 10^{-7}$ to $\sim 1.8\,82 \times 10^{-5}$ units per ml). Specimens that had levels of RT activity above the linear range of the assay were diluted in RT buffer and retested. The susceptibility of HIV-1 RT to the triphosphorylated nucleoside analogs lamivudine (3TC-TP), zalcitabine (ddC-TP), stavudine (d4T-TP), and the active form of didanosine (ddA-TP) was measured by Amp-RT based testing as previously described (Qari et al., "Susceptibility of the porcine endogenous retrovirus to reverse transcriptase and protease inhibitors," *J. Virology* 75: 1048-1053 (2001)).

Reverse Transcriptase Inhibitors (RTIs)

AZT-TP was obtained from Moravek Biochemicals, Inc. (Brea, Calif.), and ddC-TP and ddA-TP from Sigma Chemicals (St. Louis, Mo.); d4T-TP and 3TC-TP were kindly provided by Jan Balzarini (Rega Institute, Leuven, Belgium) and R. F. Schinazi (Emory University/Veterans Affairs Medical Center, Atlanta, Ga., USA), respectively. All RTIs were dissolved in dimethyl sulfoxide to make 10 mM stock. Further dilutions were made in RT buffer to achieve 0.001-50 µM final concentrations in the RT step of the Amp-RT reactions.

Reference WT and Drug-resistant Viruses

Four HIV-1 isolates derived from molecular infectious clones containing WT RT, HIV-1 SUM9xxHIV-1LAI, HIV-1HXB2, and HIV-1xxBRUpitt were used as reference WT HIV-1 isolates (Shirasaka et al., "Emergence of human immunodeficiency virus type 1 variants with resistance to multiple dideoxynucleosides in patients receiving therapy with dideoxynucleosides," *Proc. Nat. Acad. Sci. U.S.A.* 92: 2398-2402 (1995); Nguyen et al., "Resistance of human immunodeficiency virus type 1 to acyclic 6-phenylselenenyl- and 6-phenylthiopyrimidines," *Antimicrobial Agents and Chemotherapy* 38:2409-2414 (1994); Schinazi et al., "Selective inhibition of human immunodeficiency viruses by racemates and enantiomers of cis-5-fluoro-1-[2-(hydroxymethyl)-1,3-oxathiolan-5-yl] cytosine," *Antimicrobial Agents and Chemotherapy* 36: 2423-2431 (1992)). HIV-1 isolates derived from three molecular infectious clones containing from one to five MNR mutations were used as reference viruses which have different levels of resistance; HIV-1SUM8 (Q151M) has a low-level of resistance, while HIV-1SUM12 (F77L, F116V, Q151M) and HIV-1SUM13 (A62V, V75I, F77L, F116Y, Q151M) have higher levels of resistance (Ueno et al., "Enzymatic characterization of human immunodeficiency virus type 1 reverse transcriptase resistant to multiple 2',3'-dideoxynucleoside 5'-triphosphates," *J. Biol. Chem.* 270: 23605-23611 (1995); Shirasaka et al., "Emergence of human immunodeficiency virus type 1 variants with resistance to multiple dideoxynucleosides in patients receiving therapy with dideoxynucleosides," *Proc. Nat. Acad. Sci.*

U.S.A. 92: 2398-2402 (1995)). HIV-1 isolates used with classical AZT resistance mutations included HIV-1RTMF/MT-2 (T21SY), HIV-1RTMDR1/MT-2 (M41L, L74V, V106A, T215Y), and HIV-1RTMC/MT-2 (D67N, K70R, T215F, K219Q) (Larder et al., "HIV with reduced sensitivity to zidovudine (AZT) isolated during prolonged therapy," *Science* 243: 1731-1734 (1989)). Lamivudine-resistant HIV-1 M184Vpitt, nevirapine-resistant HIV-1181C/YEU, and lamivudine-nevirapine-resistant HIV-1Y181C/M184V were also included (Larder et al., "HIV with reduced sensitivity to zidovudine (AZT) isolated during prolonged therapy," *Science* 243: 1731-1734 (1989); Schinazi et al., "Selective inhibition of human immunodeficiency viruses by racemates and enantiomers of cis-5-fluoro-1-[2-(hydroxymethyl)-1,3-oxathiolan-5-yl]cytosine," *Antimicrobial Agents and Chemotherapy* 36: 2423-2431 (1992)). A well characterized plasma sample, HIV-1R598 with AZT resistance mutations (D67N, V106A, L214W, L214F, and T215Y) was also included in the panel of HIV-1 specimens. This specimen has 100-fold reduced susceptibility to AZT using a recombinant virus assay (Adje et al., "High prevalence of genotypic and phenotypic HIV-1 drug-resistant strains among patients receiving antiretroviral therapy in Abidjan, Cote d'Ivoire," *J. Acquired Immune Deficiency Syndromes* 26: 501-506 (2001)).

Plasma Specimens and Viral Stocks

Four groups of archived HIV-1 specimens with known genotypes were selected for assay validation. These included WT, MNR, MNR carrying unrelated resistance mutations, and non-MNR specimens carrying classical AZT resistance mutations (Schmit et al., "Multiple drug resistance to nucleoside analogues and nonnucleoside reverse transcriptase inhibitors in an efficiently replicating human immunodeficiency virus type 1 patient strain," *J. Infect. Dis.* 174: 962-968 (1996); Winters et al., "A 6-base pair insert in the reverse transcriptase gene of human immunodeficiency virus type 1 confers resistance to multiple nucleoside inhibitors," *J. Clin. Invest.* 102: 1769-1775 (1998); Adje et al., "High prevalence of genotypic and phenotypic HIV-1 drug-resistant strains among patients receiving antiretroviral therapy in Abidjan, Cote d'Ivoire," *J. Acquired Immune Deficiency Syndromes* 26: 501-506 (2001); Weinstock et al., "Prevalence of mutations associated with reduced antiretroviral drug susceptibility among human immunodeficiency virus type 1 seroconverters in the United States, 1993-1998," *J. Infect. Dis.* 182: 330-333 (2000)). Forty-four samples were selected which comprised 7 viral stocks and 37 plasma samples obtained from 34 HIV-1-infected persons. The viral stocks included 4 sequential isolates collected at different intervals during a 3-year period from an individual treated with AZT, zalcitabine, didanosine, stavudine, lamivudine and loviride (Schmit et al., "Multiple drug resistance to nucleoside analogues and nonnucleoside reverse transcriptase inhibitors in an efficiently replicating human immunodeficiency virus type 1 patient strain," *J. Infect. Dis.* 174: 962-968 (1996)). Eleven plasma specimens were from recent seroconverters, all of whom had WT genotypes. Twenty plasma specimens and 3 viral isolates contained several different combinations of MNR mutations. Five plasma specimens had classical AZT-resistant mutations including T215F/Y. Five specimens, including 3 viral stocks, contained T69S-insertions along with different resistance-related mutations. Viral loads were available on 12 specimens and ranged from 4,700 to 3,429,179 (median 165,000) RNA copies per ml.

Results

Assay Validation on Reference HIV-1

Amp-RT $IC_{50}$ and $IC_{90}$ values of AZT-TP and $IC_{50}$ values of other NRTIs for WT and drug-resistant HIV-1 reference viruses are shown in Table 7. Compared to WT HIV-1 all three MNR HIV-1 had reduced enzymatic susceptibility to AZT-TP, ranging from 5-fold in HIV-1SUM8 containing Q151M to 22- and 36-fold for HIV-1SUM12 and HIV-1SUM13, respectively, that contained additional MNR mutations. All three MNR isolates also showed resistance to d4T-TP, 3TC-TP, ddC-TP, and ddA-TP. In contrast, both samples containing classical AZT resistance mutations (HIV-1RTMC/MT-2 and HIV-1R598) had $IC_{50}$ and $IC_{90}$ values that were similar to those of WT HIV-1. These results demonstrate that enzymatic resistance to AZT-TP distinguishes NMR phenotype from both WT and classical AZT-resistant HIV-1 RT.

The $IC_{50}$ values of AZT-TP for WT and MNR reference viruses determined by the Amp-RT assay were compared with previously reported $IC_{50}$ values determined by a conventional RT assay and a culture-based phenotypic assay (Ueno et al., "Enzymatic characterization of human immunodeficiency virus type 1 reverse transcriptase resistant to multiple 2',3'-dideoxynucleoside 5'-triphosphates," *J. Biol. Chem.* 270: 23605-23611 (1995); Shirasaka et al., "Emergence of human immunodeficiency virus type 1 variants with resistance to multiple dideoxynucleosides in patients receiving therapy with dideoxynucleosides," *Proc. Nat. Acad. Sci. U.S.A.* 92: 2398-2402 (1995)). As shown in Table 8, phenotypic results of these three assays correlated with each other, although the fold changes seen with culture-based assays for viruses with MNR mutations were higher than those seen using both RT assays.

Assay Evaluation on Patient Specimens

The $IC_{50}$ values of AZT-TP for four sequential isolates from a patient (nos. 12-15) were determined (these results are shown in Table 8). As compared to baseline WT specimen 12, the $IC_{50}$ values for specimens 13-15 were higher, demonstrating an MNR phenotype. The results obtained are correlated with the genotypes of the specimens. These results also correlated with those determined for the respective plasma specimens L1, L2, L4, and L6 by a culture-based drug resistance assay (Table 8) (Schmit et al., "Multiple drug resistance to nucleoside analogues and nonnucleoside reverse transcriptase inhibitors in an efficiently replicating human immunodeficiency virus type 1 patient strain," *J. Infect. Dis.* 174: 962-968 (1996)).

The $IC_{50}$ values of AZT-TP for plasma specimen (no. 25) that had RT genotype A62V, S68G, V75I, F77L, F116Y, Q151M was also determined. Compared to reference WT HIV-1 isolates the $IC_{50}$ value for this specimen was 44-fold higher, a level of resistance comparable to that seen with HIV-1SUM13 that has similar MNR mutations. $IC_{50}$ and $IC_{90}$ values of a specimen (no. 40) containing T215Y and T69S-EA insertions were 0.4 and 1 μM, respectively. These values were similar to those of WT HIV-1, indicating a WT phenotype for AZT in the Amp-RT-based testing. As expected, this specimen had 100-fold reduced susceptibility to AZT using a recombinant virus assay (Winters et al., "A 6-base pair insert in the reverse transcriptase gene of human immunodeficiency virus type 1 confers resistance to multiple nucleoside inhibitors," *J. Clin. Invest.* 102: 1769-1775 (1998)).

These results demonstrate that the detection of resistance to AZT-TP in the Amp-RT-based assay is associated with HIV-1 carrying the Q151M mutation in RT.

Assay for Rapid Screening for MNR HIV-1 RT

One goal of this study was to develop a simple screening assay for MNR HIV-1 which requires testing with only one concentration of AZT-TP. As shown in Table 7, it was shown that the AZT-TP $IC_{90}$ value for WT or 215Y/F containing mutant RT ranged from 0.9-1 μM. Thus, the use of 1 μM AZT-TP was evaluated in assays for the purpose of screening for MNR RT. Table 9 shows the results of such testing on reference MNR and non-MNR viruses. For all non-MNR HIV-1, including WT or viruses that are resistant to AZT (T215Y/F), lamivudine (M184V), or nevirapine (Y181C), RT activity was inhibited by 1 µM AZT-TP, with inhibition >90%. In contrast, the RT activity of all MNR viruses was resistant to inhibition by 1 µM AZT-TP and showed <27% inhibition. These results demonstrate that 1 µM AZT-TP can be used to specifically screen for MNR HIV-1. 80% inhibition of RT activity was selected as a cut-off value for determining whether the RT of a particular virus was inhibited as this was the lowest level of inhibition observed among 39 readings of reference WT HIV-1.

After determining that the assays could be used to specifically screen for MNR HIV-1 under the above conditions, it was evaluated whether 1 µM AZT-TP could reliably be used to distinguish between WT and MNR HIV-1 RT tested at different levels of input RT activity. It was determined that it could be used. Specifically, it was determined that 1 µM AZT-TP resulted in >85% inhibition of ~$1.882 \times 10^{-7}$ to ~$1.882 \times 10^{-5}$ units of RT activity per ml from WT HIV-1 (HIV-1SUM9). These amounts of RT activities are equivalent to ~$1.96 \times 10^3$ to ~$1.96 \times 10^5$ particles of HIV-1 VQA per ml (Garcia Lerma et al., "Measurement of human immunodeficiency virus type 1 plasma virus load based on reverse transcriptase (RT) activity: evidence of variabilities in levels of virion-associated RT," *J. Infect. Dis.* 177: 1221-1229 (1998)). There was <15% inhibition of HIV-1SUM12 and HIV-1SUM13, and 50% inhibition of HIV-1SUM8 within ~$1.882 \times 10^{-7}$ to ~$1.882 \times 10^{-5}$ units of RT activity per ml. These results demonstrate the ability of the screening assay to distinguish between WT and MNR RT within a 3-$\log_{10}$ range of input RT.

To determine the detection threshold of the assay for MNR RT in a mixture with WT viruses, WT HIV-1SUM9 and MNR HIV-1SUM13 were mixed at different proportions (10-90%) and tested for the level of inhibition by 1 µM AZT-TP. Both isolates were adjusted to similar levels of RT activity before virus mixtures were prepared. While 91% inhibition of activity was observed for WT RT, only 17% inhibition was seen in the mixture containing 10% MNR HIV-1. No inhibition was noted when the mixture contained 30% or more of MNR HIV-1. These observations demonstrate an assay detection threshold for HIV-1SUM13-like resistant viruses of ~10%.

Testing of Patient Specimens

The performance of the assay was further validated by testing 37 plasma specimens from HIV-1 infected patients and 7 patient-derived viruses and the results are shown in Table 10. Analysis of four sequential patient-derived specimens (nos. 12-15) showed evidence of increasing resistance to AZT-TP, as inhibition of RT activity decreased from 100% to 40%, 6%, and 0% in Amp-RT reactions containing 1 µM AZT-TP (Table 10). The level of resistance correlated with the genotypes of the specimens as well as with the results obtained by a culture-based assay (Table 8).

The RT activity from all 12 specimens with WT genotype was inhibited (93%) by 1 µM AZT-TP, indicating a WT phenotype. In contrast, the level of RT activity inhibition from 23 specimens with MNR genotypes varied from 0-62% depending on the number and combinations of MNR-related mutations. HIV-1 RTs that had more MNR-related mutations were the least susceptible to inhibition by AZT-TP, showing inhibition ranging from 0-16% (Table 10).

The presence of either the lamivudine-resistance mutation (M184V) or nevirapine-resistance mutation (Y181C) in specimens 29-34 along with the Q151M mutation did not interfere with the detection of the MNR phenotype, as all these specimens had evidence of resistance to AZT-TP. Similarly, resistance to AZT-TP was also detectable in specimen 35 which has both the Q151M and T215Y mutations in the RT. Like WT specimens, the RT activity of 9 specimens containing classical AZT-resistant mutations was inhibited by 87% with 1 µM AZT-TP. These included 5 specimens (nos. 40-44) containing the T215Y and insertions T69S EA or SS or SG. These results demonstrate that the detection of resistance to AZT-TP in this assay is associated with HIV-1 carrying Q151M, indicating that this testing approach can easily differentiate MNR HIV-1 from non-MNR HIV-1 in plasma specimens including those with the T215Y mutation.

Discussion

Developing rapid and simple drug resistance assays is becoming more critical as drug resistance testing is increasingly integrated into patient management. The novel strategy described in Examples 1 and 2 also one to test for drug resistance based on measuring the susceptibility of plasma RT activity to RT inhibitors (Garcia Lerma et al., "A rapid non-culture-based assay for clinical monitoring of phenotypic resistance of human immunodeficiency virus type 1 to lamivudine (3TC)," *Antimicrobial Agents and Chemotherapy* 43: 264-270 (1999); Vazquez-Rosales et al., "Rapid screening of phenotypic resistance to nevirapine by direct analysis of HIV type 1 reverse transcriptase activity in plasma," *AIDS Research and Human Retroviruses* 15: 1191-1200 (1999)). However, in this example, the assay allows one to specifically detect Q151M-associated MNR R HIV-1. The assay takes advantage of the different biochemical mechanisms for AZT-resistance conferred by either Q151M or T215Y/F mutations and the inability of conventional RT assays to detect T215Y/F-associated AZT resistance (Mas et al., "Role of a dipeptide insertion between codons 69 and 70 of HIV-1 reverse transcriptase in the mechanism of AZT resistance," *EMBO J.* 19: 5752-5761 (2000); Lennerstrand et al., "Correlation between viral resistance to zidovudine (AZT) and resistance at the reverse transcriptase level found for a panel of HIV-1 mutants," *J. Virology* 75: 7202-7205 (2001); Lacey et al., "Biochemical studies on the reverse transcriptase and RNase H activities from human immunodeficiency virus strains resistant to 3'-azido-3'-deoxythymidine," *J. Biol. Chem.* 267: 15789-15794 (1992); Carroll et al., "Sensitivity of HIV-1 reverse transcriptase and its mutants to inhibition by azidothymidine triphosphate," *Biochemistry* 33: 2113-2120 (1994); Kerr et al., "Pre-steady-state kinetic characterization of wild type and 3'-azido-3'-deoxythymidine (AZT) resistant human immunodeficiency virus type 1 reverse transcriptase: implication of RNA directed DNA polymerization in the mechanism of AZT resistance," *Biochemistry* 36:14064-14070 (1997); Krebs et al., "Single-step kinetics of HIV-1 reverse transcriptase mutants responsible for virus existence to nucleoside inhibitors zidovudine and 3-TC," *Biochemistry* 36:10292-10300 (1997)). The new assay described here in Example 3 uses enzymatic resistance to AZT-TP as a diagnostic biochemical marker of the Q151M-associated MNR phenotype. As shown in the results described here, this Amp-RT-based assay has been validated on reference MNR and non-MNR HIV-1. Also, the results described here demonstrate that MNR viruses have reduced susceptibility to AZT-TP. Further, it was determined that higher levels of resistance to AZT-TP is found viruses containing several MNR-associated mutations than is found in viruses carrying Q151M alone. This more severe level of resistance in viruses containing more than the Q151M mutation is consistent with previous data (Ueno et al., "Enzymatic characterization of human immunodeficiency virus type 1 reverse transcriptase resistant to multiple 2',3'-dideoxynucleoside 5'-triphosphates," *J. Biol. Chem.* 270: 23605-23611 (1995); Suirasaka et al., "Emergence of human immunodeficiency virus type 1 variants with resistance to multiple dideoxynucleosides in patients receiving therapy with dideoxynucleosides," *Proc. Nat. Acad. Sci. U.S.A.* 92: 2398-2402 (1995)).

Validity of the assay is also supported by a good correlation between the results of this assay and those obtained by using a conventional non-PCR-based RT assay and a standard culture-based assay, although the fold changes seen in the RT assays were generally found to be lower than those seen in culture-based assays for viruses with multiple MNR mutations. The results obtained using the assay also show that all non-MNR viruses, including those with the 215Y/F mutations, had WT susceptibility to AZT-TP. This demonstrates the ability of the assay to distinguish between MNR and non-MNR viruses. The observed WT susceptibility to AZT-TP in mutant RT with 215Y/F was expected since the Amp-RT testing conditions were not modified in any way to allow measurement of AZT unblocking, which represents the primary underlying mechanism of AZT resistance in these mutants (Mas et al., "Role of a dipeptide insertion between codons 69 and 70 of HIV-1 reverse transcriptase in the mechanism of AZT resistance," *EMBO J.* 19: 5752-5761 (2000); Arion et al., "Phenotypic mechanism of HIV-1 resistance to 3'-azido-3'-deoxythymidine (AZT): increased polymerization processivity and enhanced sensitivity to pyrophosphate of the mutant viral reverse transcriptase," *Biochemistry* 37: 15908-15917 (1998); Meyer et al., "A mechanism of AZT resistance: an increase in nucleotide-dependent primer unblocking by mutant HIV-1 reverse transcriptase," Mol. Cell 4:35-43 (1999); Lennerstrand et al., "Correlation between viral resistance to zidovudine (AZT) and resistance at the reverse transcriptase level found for a panel of HIV-1 mutants," *J. Virology* 75: 7202-7205 (2001)).

To simplify this testing further, a screening assay that relies on the use of a single drug concentration was developed and validated. This assay has been evaluated on both reference viruses and on plasma samples from patients infected with MNR and non-MNR HIV-1. In the evaluation, it is shown that by using 1 µM AZT-TP, the assay successfully distinguishes MNR specimens from all non-MNR specimens including those containing classical AZT resistance-related mutations or T69S-insertions. The specificity of this assay was not compromised by the presence of unrelated resistance mutations such as Y181C or M184V, and the validation data indicated that the assay is accurate within a wide range of input RT levels. The ability of this test to detect low-level resistance related to Q151M is only noteworthy because it will allow for the early detection of MNR virus, before a highly resistant virus with a full set of additional MNR mutations develops. Taken together, these data support the use of this screening assay for the rapid detection of MNR virus in plasma.

The use of AZT-triphosphate as a single marker for MNR has simplified this testing approach further because it has eliminated the need for testing multiple NRTIs as is currently required in culture-based phenotypic assays to identify MNR viruses. Furthermore, this testing requires only 1-2 days and, therefore, is very rapid. The assay has additional advantages. For example, the ability to directly measure drug susceptibility of HIV-1 RT in plasma with little or no processing of specimens minimizes risks for selection biases. Significant potential biases are associated with many other drug resistance assays, particularly those that include complex procedures such as PCR amplification of HIV-1 RNA and generation of recombinant viruses as all such processes are inherently selective.

In conclusion, the data demonstrates that the described RT-based assay provides a simple, rapid, and inexpensive tool for the specific identification of the Q151M-associated MNR phenotype in plasma.

TABLE 7

Susceptibility of the enzymatic activity of WT, classical AZT-resistant, and MNR HIV-1 RT to various RT inhibitors. $IC_{50}$ and $IC_{90}$ values (µM) were determined by using the Amp-RT assay.

| Virus (Mutations) | AZT-TP $IC_{50}$ | AZT-TP $IC_{90}$ | d4T-TP $IC_{50}$ | ddC-TP $IC_{50}$ | 3TC-TP $IC_{50}$ | ddA-TP $IC_{50}$ |
|---|---|---|---|---|---|---|
| WT HIV-1 | | | | | | |
| HIV-1$_{SUM9}$ | 0.5 | 1 | 0.055 | 0.5 | 0.4 | 0.27 |
| HIV-1$_{LAI}$ | 0.5 | 0.9 | 0.015 | 0.5 | ND | ND |
| HIV-1HXB2 | 0.5 | 0.9 | ND | ND | ND | ND |
| HIV-1xxBRU$_{pitt}$ | ND | ND | ND | ND | 0.6 | 0.1 |
| Classical AZT-resistant HIV-1 | | | | | | |
| HIV-1$_{RTMC}$/MT2 (D67N, K70R, T215F, K219Q) | 0.5 | 1 | ND | ND | ND | ND |
| HIV-1 R598 (D67N, V106A, L210W, L214F, T215Y) | 0.5 | 1 | ND | ND | ND | ND |
| MNR HIV-1 | | | | | | |
| HIV-1$_{SUM8}$ (Q151M) | 2.5 (5)* | 4.5 (4.7) | 0.32 (9.1) | 1.8 (3.6) | 0.9 (1.8) | 1.2 (6.5) |
| HIV-1$_{SUM12}$ (F77L, F116Y, Q151M) | 11 (22) | 18 (18.6) | 0.37 (10.6) | 6 (12) | 2.7 (5.4) | 1.1 (5.9) |
| HIV-1$_{SUM13}$ (A62V, V75I, F77L, F116Y, Q151M) | 18 (36) | 45 (46.6) | 0.37 (10.6) | 7.5 (15) | 3.3 (6.6) | 6 (32.4) |

*fold resistance as compared to the mean IC values of WT HIV-1.
$IC_{50}$ and $IC_{90}$ values were calculated from triplicate results.

TABLE 8

AZT susceptibility measurements determined by the Amp-RT assay, a conventional RT assay, and culture-based tests.

| Specimens | Mutations | IC$_{50}$ in μM (fold)* | | |
|---|---|---|---|---|
| | | Amp-RT assay | RT assay[#] | Culture based assay[¶] |
| Reference viruses (Ueno et al., 1995; Shirasaka et al., 1995) | | | | |
| HIV1$_{SUM9}$ | None | 0.5 | 0.023 | 0.5 |
| HIV1$_{SUM8}$ | Q151M | 2.5 (5) | 0.19 (8.3) | 5 (10) |
| HIV1$_{SUM12}$ | F77L, F116Y, Q151M | 11 (22) | 0.88 (38) | >160 (>320) |
| HIV1$_{SUM13}$ | A62V, V75I, F77L, F116Y, Q151M | 18 (36) | 1.5 (65) | >160 (>320) |
| Patient-derived viruses (Schmit et al., 1996) | | | | |
| 12 (L1) | None | 0.35 | ND | 0.006 |
| 13 (L2) | S68G, Q151M | 1.35 (3.9) | ND | 0.009 (1.5) |
| 14 (L4) | A62A/V, S68G, V75I, F77L, F116Y, Q151M | 8.23 (23.5) | ND | 3.8 (633) |
| 15 (L6) | S68G, V75I, F77L, K103N, F116Y, Q151M M184V | 14.65 (41.8) | ND | 18.7 (3117) |

*Fold change from IC$_{50}$ values of WT HIV-1.
[#]RT-Mediated polymerase activity (Ueno et al., 1995).
[¶]Inhibition of HIV-1- induced cytopathic effect for testing reference viruses and plaque reduction assay for testing plasma specimens (Schmit et al., 1996; Shirasaka et al., 1995).

TABLE 9

Levels of RT activity inhibition of reference HIV-1 isolates by 1 μM AZT-TP.

| Reference viruses | Mutations | % inhibition* (SEM) |
|---|---|---|
| Non-MNR phenotype | | |
| HIV-1$_{SUM9}$ | WT | 95.8 (±1.4) |
| HIV-1$_{LAI}$ | WT | 99.9 (±0.02) |
| HIV-1$_{HXB2}$ | WT | 98 (±2) |
| HIV-1xxBRU$_{pitt}$ | WT | 93.5 (±6.5) |
| HIV-1$_{RTMF}$/MT-2 | T215Y | 96 (±4) |
| HIV-1$_{RTMDRI}$/MT-2 | M41L, L74V, V106A, T215Y | 94.6 (±5.4) |
| HIV-1$_{RTMC}$/MT-2 | D67N, K70R, T215F, K219Q | 91.5 (±8.5) |
| HIV-1R598 | D67N, V106A, L210W, L214F, T215Y | 97.8 (±2.2) |
| HIV-1181C/Y$_{EU}$ | Y181C | 93.5 (±4.2) |
| HIV-1M184V$_{pitt}$ | M184V | 91.1 (±3.3) |
| HIV-1$_{Y181C/M184V}$ | Y181C, M184V | 94.4 (±3) |
| MNR phenotype | | |
| HIV-1$_{SUM8}$ | Q151M | 26.6 (±6.1) |
| HIV-1$_{SUM12}$ | F77L, F116V, Q151M | 13.1 (±5.5) |
| HIV-1$_{SUM13}$ | A62V, V75I, F77L, F116Y, Q151M | 12.9 (±2.8) |

*Average of 2 to 13 tests done in duplicate.
SEM, Standard error of the mean.

TABLE 10

Direct detection of HIV-1 MNR phenotype in plasma and patient-derived isolates by inhibition with 1 μM AZT-TP in the Amp-RT assay.

| Specimens* | Mutations | % inhibition[#] | Phenotype[¶] |
|---|---|---|---|
| Recent seroconverters | | | |
| 1-11 | WT | 93-100 | S |
| Sequential specimens from one patient | | | |
| 12 | WT | 100 | S |
| 13 | S68G, Q151M | 40 | R |
| 14 | A62A/V, S68G, V75I, F77L, F116Y, Q151M | 6 | R |
| 15 | S68G, V75I, F77L, K103N, F116Y, Q151M, M184V | 0 | R |
| MNR specimens | | | |
| 16 | Q151Q/M | 38 | R |
| 17, 18 | Q151M | 23, 57 | R |
| 19-21 | A62V, V75I, F77L, F116Y, Q151M | 4-16 | R |
| 22-25 | A62V, S68G, V75I, F77L, F116Y, Q151M | 0 | R |

TABLE 10-continued

Direct detection of HIV-1 MNR phenotype in plasma and patient-derived isolates by inhibition with 1 µM AZT-TP in the Amp-RT assay.

| Specimens* | Mutations | % inhibition# | Phenotype¶ |
|---|---|---|---|
| 26 | A62V, V75T, Q151M, M184I/M | 11 | R |
| 27-28 | V75I, F77L, F116Y, Q151M | 0, 8 | R |
| | MNR specimens carrying unrelated resistance mutations | | |
| 29 | A62V, V75I, F77L, F116Y, Q151M, M184V | 0 | R |
| 30 | K65R, K70R, V75I, F77L, F116Y, Q151M | 13 | R |
| 31 | D67N, Q151M, M184V | 17 | R |
| 32 | V75I, F77L, F116Y, Q151M, M184V | 26 | R |
| 33, 34 | A62V, K70G, Q151M, Y181C, M184V | 39.5, 45 | R |
| 35 | F116Y, Q151M, T215Y, V35I, I135T | 62 | R |
| | Non-MNR specimens carrying other resistance mutations | | |
| 36 | D67N, L210W, L214F, T215Y | 95.6 | S |
| 37 | A62V, K70R, L74V, K103N, T215F | 92.6 | S |
| 38 | D67N, T69D, Y181C, L214F, T215Y | 90 | S |
| 39 | M41L, M184V, L214F, T215Y | 89.1 | S |
| 40-43 | T215Y, T69S-insertions EA/SS/SG | 87-97 | S |
| 44 | A62V, I135T, Y181C, T215Y, T69S-insertions SG | 96.5 | S |

*All specimens are plasma except #12-15, 40, 41, and 44 are patient-derived isolates
Mean of duplicate values
¶S, sensitive (non-MNR phenotype); R, resistant (MNR phenotype). Phenotype interpretation based on inhibition of RT activity by 1 µM AZT-TP.

All of the publications and references mentioned herein are hereby incorporated by reference.

Modifications and variations of the present assay and kit will be obvious to those skilled in the art from the foregoing detailed description. Such modifications and variations are intended to come within the scope of the appended claims.

The invention claimed is:

1. A method for characterizing strains of HIV-1 as being MNR mutants comprising:

incubating a strain of HIV-1 with a single concentration of a reverse transcriptase inhibitor consisting of: an $IC_{50}$ or $IC_{90}$ concentration of AZT-TP for a wild-type strain of HIV-1, an RNA template, and a first complementary DNA primer, and characterizing a HIV-1 strain as being an MNR mutant by detecting the relative presence or relative absence of a first DNA product, wherein the detection of the first DNA product indicates that the strain of HIV-1 is an MNR mutant strain.

2. The method of claim 1 wherein the RNA template and first complementary DNA primer are oligonucleotides that comprise sequence consisting essentially of sequence from a region of the encephalomyocarditis virus genome having no significant secondary structure and less than 50% G-C content.

3. The method of claim 2 wherein the RNA template is an oligonucleotide having the sequence set forth in SEQ ID NO: 4.

4. The method of claim 2 wherein the first complementary DNA primer is an oligonucleotide having the sequence set forth in SEQ ID NO: 2.

5. The method of claim 2 wherein the DNA product is detected by hybridization to a detectable hybridization probe, wherein the hybridization probe is an oligonucleotide having the sequence set forth in SEQ ID NO: 3.

6. The method of claim 1 further comprising incubating the strain of HIV-1, RNA template and first complementary DNA primer with a second complementary DNA primer comprising sequence from the encephalomyocarditis virus genome, wherein the second complementary DNA primer is extended during amplification to form a second DNA product.

7. The method of claim 4 wherein the second complementary DNA primer is an oligonucleotide having the sequence set forth in SEQ ID NO: 1.

8. The method of claim 1 further comprising contacting the first DNA product with a second functionally complementary DNA primer comprising sequence consisting essentially of sequence from the encephalomyocarditis virus genome, wherein the second functionally complementary DNA primer is extended to form a second DNA product.

9. A method for detecting an MNR mutant strain in a sample, consisting essentially of:

incubating a first sample comprising a strain of HIV-1 with a single quantity of AZT-TP, an RNA template, and a first complementary DNA primer to produce a first amount of a DNA product;

incubating a second sample comprising wild-type or a non-MNR mutant strain of HIV-1, with the single quantity of AZT-TP, an RNA template, and a first complementary DNA primer to produce a second amount of a DNA product; and characterizing a HIV-1 strain as being an MNR mutant by detecting a difference between the first amount of a DNA product and the second amount of a DNA product, wherein a greater first amount of the DNA product indicates that the first sample comprises an MNR mutant strain of HIV-1.

10. The method of claim 9 wherein the first sample comprises an MNR strain of HIV-1 and a wild-type or non-MNR mutant strain of HIV-1.

11. A method for characterizing strains of HIV-1 as being MNR mutants, comprising:

incubating a strain of HIV-1 with a single concentration of a reverse transcriptase inhibitor consisting of: an $IC_{50}$ or $IC_{90}$ concentration of AZT-TP for a wild-type strain of HIV-1, an RNA template, and a first complementary DNA primer, wherein the RNA template and first complementary DNA primer are oligonucleotides from a region of the encephalomyocarditis virus genome having no significant secondary structure and less than 50% G-C content, wherein the RNA template directs the synthesis of a first DNA product, and characterizing a HIV-1 strain as being an MNR mutant by detecting the relative presence or relative absence of the first DNA product, wherein the detection of the first DNA product indicates that the strain of HIV-1 is MNR mutant strain comprising a Q151M mutation and not a wild-type strain or a mutant HIV-1 strain selected from the group consisting of: T215Y, M41L, L74V, V106A, D67N, K70R, K219Q, M184V, Y181C, L210W, L214F, A62V, K103N, T215F, T69D, T69S insertions EA/SS/SG, I1351T and Y181C.

12. A method for characterizing strains of HIV-1 as being MNR mutants, comprising:

incubating a strain of HIV-1 with a single concentration of a reverse transcriptase inhibitor consisting of: an $IC_{50}$ or $IC_{90}$ concentration of AZT-TP for a wild-type strain of HIV-1 or a 215Y/F mutant HIV-1 strain, an RNA template, and a first complementary DNA primer, wherein the RNA template and first complementary DNA primer are oligonucleotides from a region of the encephalomyocarditis virus genome having no significant secondary structure and less than 50% G-C content, wherein the RNA template directs the synthesis of a first DNA product, and characterizing a HIV-1 strain as being an MNR mutant by detecting the relative presence or relative absence of the first DNA product, wherein the detection of the first DNA product indicates that the strain of HIV-1 is MNR mutant strain comprising a Q151M mutation and not a wild-type strain or a mutant HIV-1 strain selected from the group consisting of: : T215Y, M41L, L74V, V106A, D67N, K70R, K219Q, M184V, Y181C, L210W, L214F, A62V, K103N, T215F, T69D, T69S insertions EA/SS/SG, I135T and Y181C.

13. The method of claim 11 further comprising contacting the first DNA product with a second functionally complementary DNA primer comprising sequence consisting essentially of sequence from the encephalomyocarditis virus genome, wherein the second functionally complementary DNA primer is extended to form a second DNA product.

14. The method of claim 12 further comprising contacting the first DNA product with a second functionally complementary DNA primer comprising sequence consisting essentially of sequence from the encephalomyocarditis virus genome, wherein the second functionally complementary DNA primer is extended to form a second DNA product.

15. The method of claim 9 further comprising contacting the first DNA product with a second functionally complementary DNA primer comprising sequence consisting essentially of sequence from the encephalomyocarditis virus genome, wherein the second functionally complementary DNA primer is extended to form a second DNA product.

* * * * *

UNITED STATES PATENT AND TRADEMARK OFFICE
CERTIFICATE OF CORRECTION

PATENT NO. : 7,691,572 B2
APPLICATION NO. : 11/054023
DATED : April 6, 2010
INVENTOR(S) : Walid M. Heneine et al.

It is certified that error appears in the above-identified patent and that said Letters Patent is hereby corrected as shown below:

Col. 4, line 6: replace "complementary" with --complementarity--;
Col. 9, line 51: replace "fonied" with --formed--;
Col. 9, line 51: replace "dnig" with --drug--;
Col. 10, line 19: replace "complementary" with --complementarity--;
Col. 18, line 63: replace "Anmp-RT" with --Amp-RT--;
Col. 19, lines 39-40: replace "transcliptase" with --transcriptase--;
Col. 19, line 41: replace "inlibited" with --inhibited--;
Col. 24, line 57: replace "inidbition" with --inhibition--;
Col. 25, line 57: replace "activity form" with --activity from--;
Col. 28, line 12: replace "treatmeant" with --treatment--;
Col. 28, line 16: replace "RT inlhibitionl" with --RT inhibition--;
Col. 28, line 33: replace "bad high levels" with --had high levels--;
Col. 28, line 35: replace "MUT/GINR" with --MUT/GNR--;
Col. 38, line 11: replace "NMR" with --MNR--;
Col. 40, line 31: replace "MNR R HIV-1" with --MNR HIV-1--.

Signed and Sealed this

Fifth Day of October, 2010

David J. Kappos
*Director of the United States Patent and Trademark Office*